(12) United States Patent
Chilcote et al.

(10) Patent No.: US 7,910,333 B2
(45) Date of Patent: Mar. 22, 2011

(54) ANTIBODIES TO ALPHA-SYNUCLEIN

(75) Inventors: Tamie Chilcote, San Francisco, CA (US); Robin Barbour, Walnut Creek, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/695,085

(22) Filed: Jan. 27, 2010

(65) Prior Publication Data

US 2010/0203631 A1 Aug. 12, 2010

Related U.S. Application Data

(63) Continuation of application No. 10/984,192, filed on Nov. 8, 2004, now Pat. No. 7,674,599.

(60) Provisional application No. 60/518,140, filed on Nov. 8, 2003.

(51) Int. Cl.
*C12P 21/08* (2006.01)
*C07K 16/18* (2006.01)

(52) U.S. Cl. ............... 435/69.7; 530/387.3; 530/388.1; 530/809; 435/70.21

(58) Field of Classification Search .................. None
See application file for complete search history.

(56) References Cited

U.S. PATENT DOCUMENTS

| | | | |
|---|---|---|---|
| 4,883,666 A | 11/1989 | Sabel et al. |
| 5,576,184 A | 11/1996 | Better et al. |
| 5,589,154 A | 12/1996 | Anderson |
| 5,753,624 A | 5/1998 | McMichael |
| 5,780,587 A | 7/1998 | Potter |
| 5,851,996 A | 12/1998 | Kline |
| 5,958,883 A | 9/1999 | Snow |
| 6,504,080 B1 | 1/2003 | Van Der Putten |
| 6,710,226 B1 | 3/2004 | Schenk |
| 6,743,427 B1 | 6/2004 | Schenk |
| 6,761,888 B1 | 7/2004 | Schenk |
| 6,780,971 B2 | 8/2004 | Wolozin et al. |
| 6,787,138 B1 * | 9/2004 | Schenk |
| 6,787,139 B1 * | 9/2004 | Schenk |
| 6,787,140 B1 * | 9/2004 | Schenk |
| 6,787,143 B1 * | 9/2004 | Schenk |
| 6,787,144 B1 * | 9/2004 | Schenk |
| 6,787,523 B1 * | 9/2004 | Schenk |
| 6,858,704 B2 * | 2/2005 | Kim |
| 6,866,849 B2 * | 3/2005 | Schenk |
| 6,866,850 B2 * | 3/2005 | Schenk |
| 6,890,535 B1 * | 5/2005 | Schenk |
| 6,923,964 B1 * | 8/2005 | Schenk |
| 6,946,135 B2 * | 9/2005 | Schenk et al. |
| 6,972,127 B2 * | 12/2005 | Schenk |
| 7,014,855 B2 * | 3/2006 | Schenk |
| 7,060,464 B2 * | 6/2006 | Kim |
| 7,138,255 B2 * | 11/2006 | Vodyanoy et al. |
| 7,306,945 B2 * | 12/2007 | Chilcote et al. |
| 7,358,331 B2 * | 4/2008 | Chilcote et al. |
| 7,479,482 B2 * | 1/2009 | Frangione et al. |
| 2002/0094335 A1 | 7/2002 | Chalifour et al. |
| 2002/0151464 A1 | 10/2002 | Wolozin et al. |
| 2002/0160394 A1 | 10/2002 | Wu |
| 2002/0187157 A1 | 12/2002 | Jensen et al. |
| 2002/0197258 A1 | 12/2002 | Ghanbari et al. |
| 2003/0086938 A1 | 5/2003 | Jensen et al. |
| 2003/0165496 A1 | 9/2003 | Basi et al. |
| 2003/0166558 A1 | 9/2003 | Frangione et al. |
| 2003/0185827 A1 | 10/2003 | Rodriguez et al. |
| 2004/0136993 A1 | 7/2004 | Schenk et al. |
| 2004/0137523 A1 | 7/2004 | Vodyanoy et al. |
| 2004/0146521 A1 * | 7/2004 | Schenk et al. |
| 2004/0197831 A1 * | 10/2004 | Weksler et al. |
| 2005/0037013 A1 * | 2/2005 | Schenk et al. |
| 2005/0123544 A1 * | 6/2005 | Schenk et al. |
| 2005/0176078 A1 * | 8/2005 | Allsop et al. |
| 2005/0196818 A1 * | 9/2005 | Chilcote et al. |
| 2005/0198694 A1 * | 9/2005 | Chilcote et al. |
| 2005/0203010 A1 * | 9/2005 | Kim |
| 2005/0255113 A1 * | 11/2005 | Huston et al. |
| 2006/0058233 A1 * | 3/2006 | Schenk et al. |
| 2006/0259986 A1 * | 11/2006 | Chilcote et al. |
| 2008/0014194 A1 * | 1/2008 | Schenk et al. |
| 2008/0175838 A1 * | 7/2008 | Schenk et al. |
| 2009/0208487 A1 * | 8/2009 | Schenk et al. |

FOREIGN PATENT DOCUMENTS

| | | |
|---|---|---|
| EP | 0 613 007 A2 | 8/1994 |
| EP | 1 633 189 A2 | 3/2006 |
| WO | WO 91/16819 A1 | 11/1991 |
| WO | WO 95/06407 A1 | 3/1995 |
| WO | WO 99/06545 A2 | 2/1999 |
| WO | WO 99/06545 A3 | 2/1999 |
| WO | WO 99/27944 A1 | 6/1999 |
| WO | WO 99/40191 A1 | 8/1999 |
| WO | WO 99/50300 A1 | 10/1999 |
| WO | WO 99/60024 A1 | 11/1999 |
| WO | WO 00/18917 A2 | 4/2000 |
| WO | WO 00/18917 A3 | 4/2000 |
| WO | WO 00/72876 A2 | 12/2000 |
| WO | WO 00/72876 A3 | 12/2000 |
| WO | WO 00/72880 A2 | 12/2000 |

(Continued)

OTHER PUBLICATIONS

U.S. Appl. No. 12/528,439, filed Aug. 24, 2009, Schenk et al.
U.S. Appl. No. 11/894,772, filed Aug. 20, 2007, Schenk et al.
U.S. Appl. No. 11/894,744, filed Aug. 20, 2007, Schenk et al.
U.S. Appl. No. 11/894,605, filed Aug. 20, 2007, Schenk et al.
U.S. Appl. No. 11/841,996, filed Aug. 20, 2007, Schenk et al.
U.S. Appl. No. 11/660,015, filed Feb. 9, 2007, Schenk et al.
U.S. Appl. No. 10/850,570, filed May 19, 2004, Chilcote et al.
U.S. Appl. No. 60/518,140, filed Nov. 8, 2003, Chilcote et al.

(Continued)

*Primary Examiner* — Daniel E Kolker
(74) *Attorney, Agent, or Firm* — Alston & Bird LLP

(57) ABSTRACT

The invention provides methods for detecting alpha-synuclein. The invention also identifies preferred epitopes of alpha synuclein for use in such detection, and provides antibodies specifically binding to such epitopes.

9 Claims, 4 Drawing Sheets

FOREIGN PATENT DOCUMENTS

| | | | |
|---|---|---|---|
| WO | WO 00/72880 A3 | 12/2000 |
| WO | WO 01/06989 A2 | 2/2001 |
| WO | WO 01/06989 A3 | 2/2001 |
| WO | WO 01/53457 A2 | 7/2001 |
| WO | WO 01/53457 A3 | 7/2001 |
| WO | WO 01/60794 A2 | 8/2001 |
| WO | WO 01/60794 A3 | 8/2001 |
| WO | WO 02/03911 A2 | 1/2002 |
| WO | WO 03/000714 A2 | 1/2003 |
| WO | WO 03/000714 A3 | 1/2003 |
| WO | WO 03/045128 A2 | 6/2003 |
| WO | WO 03/045128 A3 | 6/2003 |
| WO | WO 2004/009625 A2 | 1/2004 |
| WO | WO 2004/009625 A3 | 1/2004 |
| WO | WO 2004/041067 A2 | 5/2004 |
| WO | WO 2004/041067 A3 | 5/2004 |
| WO | WO 2005/013889 A3 | 2/2005 |
| WO | WO 2005/047860 A2 | 5/2005 |
| WO | WO 2005/047860 A3 | 5/2005 |
| WO | WO 2006/020581 A2 | 2/2006 |
| WO | WO 2006/020581 A3 | 2/2006 |
| WO | WO 2006/045037 A2 | 4/2006 |
| WO | WO 2006/045037 A3 | 4/2006 |
| WO | WO 2007/011907 A2 | 1/2007 |
| WO | WO 2007/012061 A2 | 1/2007 |
| WO | WO 2007/021255 A1 | 2/2007 |
| WO | WO 2008/103472 A2 | 8/2008 |

OTHER PUBLICATIONS

U.S. Appl. No. 60/471,929, filed May 19, 2003, Chilcote et al.

U.S. Appl. No. 60/423,012, filed Nov. 1, 2002, Schenk et al.

Abbas et al., *Cellular and Molecular Immunology*, 522-523 (Elsevier Saunders) (5th Ed. Updated Ed., 2005).

Anderson et al., "Phosphorylation of SER-129 is the dominant pathological modification of alpha-synuclein in familial and sporadic Lewy body disease," The Journal of Biological Chemistry, 281:29739-29752 (2006).

Alves da Costa, "Recent Advances on α-Synuclein Cell Biology : Functions and Dysfunctions," Current Molecular Medicines, 3:17-24 (2003).

Bales et al., "Cholinergic dysfunction in a mouse model of Alzheimer disease is reversed by an anti-Aβ antibody," *J. Clin. Invest.*, 116(3):825-832 (2006).

Bard et al., "Peripherally administered antibodies against amyloid β-peptide enter the central nervous system and reduce pathology in a mouse model of Alzheimer disease," *Nature Medicine*, 6(8):916-919 (2000).

Bennett et al., "Degradation of α-Synuclein by Proteasome," *J. Biol. Chem.*, 274(48):33855-33858 (1999).

Bodles et al., "Toxicity of non-Aβ component of Alzheimer's disease amyloid, and N-terminal fragments thereof, correlates to formation of β-sheet structure and fibrils," *Eur. J. Biochem.*, 267:2186-2194 (2000).

Brooks et al., "Synuclein proteins and Alzheimer's disease," Trends Neurosci., 17(10):404-405 (1994).

Cao et al., "Development of an Alpha Synuclein Recombinant Protein as a Potential Candidate Against Parkinson's Disease," Program No. 594.3, Abstract Viewer/Itinerary Planner, Washington D.C.: Society for Neuroscience (2002).

Casadesus et al., "The Estrogen Myth; Potential Use of Gonadotropin-releasing hormone Agonists for Treatment of Alzheimer's Disease," Drugs R&D, 7(3):187-193 (2006).

Chang et al., "Adjuvant activity of incomplete Freund's adjuvant," *Advanced Drug Delivery Reviews*, 32:173-186 1998).

Chapman, "Model behaviour," *Nature*, 408:915-916 (2000).

Chen et al., "Neurodegenerative Alzheimer-like pathology in PDAPP 717V→F transgneic mice," *Progress in Brain Research*, 117:327-337 (1998).

Chilcote et al., "Comparison of alpha-synuclein species in Lewy bodies and the soluble fraction of diffuse Lewy body disease brain," Database Biosis [Online] Biosciences Information Service, Philadelphia, PA, US (2003) Abstract only.

Clayton et al., "Synucleins in Synaptic Plasticity and Neurodegenerative Disorders," *J. Neurosci. Res.*, 58:120-129 (1999).

Clayton et al, "The synucleins: a family of proteins involved in synaptic function, plasticity, neurodegeneration, and disease," *Trends Neurosci.*, 21(6):249-254 (1998).

Cleland et al., "Isomerization and Formulation Stability of the Vaccine Adjuvant QS-21," *J.of Pharm Sci.*, 85(1): 22-28 (1996).

Conway et al., "Acceleration of oligomerization, not fibrillization, is a shared property of both α-synuclein mutations linked to early-onset Parkinson's disease: Implications for pathogenesis and therapy," PNAS, 97(2):571-576 (2000).

Crowther et al., "Synthetic filaments assembled from C-terminally truncated a-synuclein," *FEBS Letters*, 436:309-312 (1998).

Culvenor et al., "Non-Aβ Component of Alzheimer's Disease Amyloid (NAC) Revisited, NAC and α-Synuclein are not Associated with Aβ Amyloid," *Am. J. Pathology*, 155(4):1173-1181 (1999).

De Lustig et al., "Peripheral markers and diagnostic criteria in Alzheimer's disease: Critical evaluations," *Rev. in Neurosci.*, 5:213-224 (1994).

Demattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).

Dictionary.com definition of "prophylactic", pp. 1-3 downloaded from internet Oct. 12, 2005.

Dictionary entry for "prophylactic", *Webster's New World Dictionary of American English*, 3rd College Edition, New York, p. 1078 (1988).

Di Monte et al., "Environmental Factors in Parkinson's Disease," *Neurotoxicology*, 23: 487-502 (2002).

Dixon, C. et al., "Alpha-Synuclein Targets the Plasma Membrane via the Secretory Pathway and Induces Toxicity in Yeast," *Genetics*, May 2005;170(1):47-59. Epub Mar. 2, 2005.

El-Agnaf et al., "α-Synuclein implicated in Parkinson's disease is present in extracellular biological fluids, including human plasma," *FASEB J.*, 17(3):1945-1947 (2003).

El-Agnaf et al., "α-Synuclein implicated in Parkinson'disease is present in extracellular biological fluids, including human plasma," *FASEB J. express article 10.1096/fj/03-0098fje*, Published online Aug. 15, 2003. Abstract.

Elan, "Elan and AHP Provide an Update on the Phase 2A Clinical Trial of AN-1792," Press Release. (Jan. 18, 2002).

Elan, "Elan and Wyeth Provide Update on Status of Alzheimer's Collaboration," Press Release (Mar. 1, 2002).

Eliezer, D. et al., "Conformational Properties of Alpha-Synuclein in its Free and Lipid-associated States," *Journal of Molecular Biology*, 307(4):1061-1073 (2001).

Ellis et al., "α-Synuclein is Phophorylated by Members of the Src Family of Protein-tyrosine Kinases," *J. Biol. Chem.*, 276(6):3879-3884 (2001).

Emadi, S. et al., "Inhibiting Aggregation of Alpha-Synuclein with Human Single Chain Antibody Fragments," *Biochemistry*, 43(10):2871-2878 (2004).

Esiri, "Is an effective immune intervention for Alzheimer's disease in prospect?", *Trends in Pharm, Sci.*, 22:2-3 (2001).

EP 04776059.0 European Supplementary Search Report completed Jun. 13, 2006.

EP 03783083.3 European Supplementary Search Report completed Oct. 10, 2008.

EP 05783732 European Supplementary Search Report completed Mar. 5, 2009.

EP 05814041.9 European Supplementary Search Report completed Oct. 29, 2008.

EP 06800177 European Supplementary Search Report completed Mar. 9, 2009.

Farrer, M.J., "Genetics of Parkinson disease: Paradigm shifts and future prospects," *Nat. Rev. Genet.*, 7:306-318 (2006).

Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).

Frenkel et al., "Immunization against Alzheimer's β-amyloid plaques via EFRH phage administration," *PNAS*, 97:11455-11459 (2000).

Frenkel et al., "N-terminal EFRH sequence of Alzheimer's β-amyloid peptide represents the epitope of its anti-aggregating antibodies," *J. of Neuroimmunology*, 88:85-90 (1998).

Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York, pp. 242-247 (1997).

Friedland et al., "Development of an anti-Aβ monoclonal antibody for in vivo imaging of amyloid angiopathy in Alzheimer's disease," *Mol. Neurology*, 9:107-113 (1994).

Games et al., "Alzheimer-type neuropathology in transgenic mice overexpressing V717F β-amyloid precursor protein," *Nature*, 373(6514):523-527 (1995).

Games et al., "Prevention and Reduction of AD-type Pathology in PDAPP Mice Immunized with Aβ$_{1-42}$," *Annals of the New York Academy of Science*, 920:274-284 (2000).

Garzon, J. et al., "Transport of CSF antibodies to G-Alpha subunits across neural membranes requires binding to the target protein and protein kinase C activity," *Molecular Brain Research*, 65(2):151-166 (1999).

Giasson et al., "A Panel of Epitope-Specific Antibodies Detects Protein Domains Distributed Throughout Human α-Synuclein in Lewy Bodies of Parkinson's Disease," Journal of Neuroscience Research, 59:528-533 (2000).

Giasson et al., "Mutant and Wild Type Human α-Synucleins Assemble into Elongated Filaments with Distinct Morphologies in Vitro," *J. Biol. Chem.*, 274(12):7619-7622 (1999).

Goldsby et al., "Vaccines," Chapter 18 from *Immunology, 4th Edition*, W.H. Freeman and Company, New York, pp. 449-465 (2000).

Goldsteins et al., "Exposure of cryptic epitopes on transthyretin only in amypoid and in amyloidogenic mutants," *PNAS*, 96:3108-3113 (1999).

Grubeck-Loebenstein, et al., "Immunization with β-amyloid: could T-cell activation have a harmful effect?", *TINS*, 23:114 (2000).

Hamburger, A.W. et al., "Isolation and characterization of monoclonal antibodies reactive with endothelial cells," *Tissue & Cell*, 17(4): 451-459 (1985).

Hansen et al., "Chapter 14: Neurobiology of Disorders with Lewy Bodies," *Functional Neurobiology of Aging*, (Hof and Mobbs, Eds.) 173-182 (2001).

Harlow et al., eds., *Antibodies, A Laboratory Manual*, Cold Spring Harbor Laboratory, p. 98 (1988).

Hartman et al., "Treatment with an Amyloid-β Antibody Ameliorates Plaque Load, Learning Deficits, and Hippocampal Long-Term Potentiation in a Mouse Model of Alzheimer's Disease," *Journal of Neuroscience*, 25:6213-6220 (2005).

Hashimoto et al., "Alpha-synuclein in Lewy Body Disease and Alzheimer's Disease," *Brain Pathology*, 9:707-720 (1999).

Hashimoto et al., "β-synuclein inhibits [alpha]-synuclein aggregation: A possible role as an anti-Parkinsonian factor", *Neuron*, 32(2):213-223 (2001).

Heiser et al., "Inhibition of huntington fibrillogenesis by specific antibodies and small molecules: Implications for Huntington's disease therapy," Proceedings of the National Academy of Sciences of USA, 97(12):6739-6744 (2000), Abstract only.

Hooper et al., *Cellular Peptidases in Immune Functions and Diseases 2*, (Langer and Ansorge, Eds., Plenum Publishers) 379-390 (2000).

Hornbeck et al., "Enzyme-Linked Immunosorbant Assays (ELISAs)," Current Protocols in Molecular Biology, 11.2.1-11.2.22 (1991).

Hoyer, W. et al., "Dependence of alpha-Synuclein Aggregate Morphology on Solution Conditions," *J. Mol. Biol.*, 322:383-393 (2002).

Hsiao, K., "From prion diseases to Alzheimer's disease," *J. Neural. Transm. Suppl.* 49:135-144 (1997).

Hsu et al., "α-Synuclein Promotes Mitochondrial Deficit and Oxidative Stress," *Am. J. Pathology*, 157(2):401-410 (2000).

Irizarry, M.C. "Nigral and cortical Lewy bodies and dystrophic nigral neurites in Parkinson's disease and cortical Lewy body disease contain α-synuclein immunoreactivity," *J. Neuropathol. Exp. Neurol.*, 57(4): 334-337 (1998).

Iwai, "Properties of NACP/alpha-synuclein and its role in Alzheimer's disease," *Molecular Basis of Disease*, 1502(1): 95-109 (2000).

Iwai et al., "The Precursor Protein of Non-Aβ Component of Alzheimer's Disease Amyloid is a Presynaptic Protein of the Central Nervous System," *Neuron*, 14:467-475 (1995).

Iwatsubo, T. et al., "Purification and Characterization of Lewy Bodies from the Brains of Patients with Diffuse Lewy Body Disease," *Am J Pathol.*, 148(5):1517-1529 (1996).

Jakes et al., "Epitope mapping of LB509, a monoclonal antibody directed against human α-synuclein," *Neurosci. Ltrs.*, 269:13-16 (1999).

Janeway et al., *Immunology*, 3$^{rd}$ edition, 8:18-8:19 (1997).

Jen, et al., "Preparation and purification of antisera against different regions or isoforms of beta-amyloid precursor protein," *Brain Research Protocols*, 2:23-30 (1997).

Jendroska et al., "Amyloid β-Peptide and the Dementia of Parkinson's Disease," *Movement Disorders*, 11(6):647-653 (1996).

Jensen et al., "Residues in the synuclein consensus motif of the alpha-synuclein fragment, NAC, participate in transglutaminase-catalysed cross-linking to Alzheimer-disease amyloid beta A4 peptide," *Biochem. J.*, 310(Pt 1):91-94 (1995).

Jobling et al., "Analysis of structure and function of the B subunit of cholera toxin by the use of site-directed mutagenesis," *Molecular Microbiology*, 5(7):1755-1767 (1991).

Kim, T. D. et al., "Structural and Functional Implications of C-Terminal Regions of α-Synuclein," *Biochemistry*, 41:13782-13790 (2002).

Kim, T.D. et al., "Structural Changes in α-Synuclein Affect its Chaperone-like Activity in Vitro," *Protein Science*, 9:2489-2496 (2000).

Kotzbauer et al., "Lewy Body Pathology in Alzheimer's Disease," *Journal of Molecular Neuroscience*, 17(2): 225-232 (2001).

Kuby, J., eds., *Immunology*, pp. 92-97 and 110 (W.H. Freeman & Co., New York) (3rd Edition, 1997).

Kuby J., eds., *Immunology*, pp. 92-97 and 131 (W.H. Freeman & Co., New York) (3rd Edition, 1997).

Kuby J., eds., *Immunology*, pp. 156-158 (W.H. Freeman & Co., New York) (3rd Edition, 1997).

Lansbury Jr., P. T., "Evolution of amyloid: What normal protein folding may tell us about fibrillogenesis and disease," *Proc Natl Acad Sci*, 96(7): 3342-3344 (1999).

Lecerf et al., "Human single-chain Fv intrabodies counteract in situ huntingtin aggregation in cellular models of Huntington's disease," Proceeding of the National Academy of Sciences of USA, 98(8):4764-4769 (2001).

Lee et al., "Formation and Removal of α-Synuclein Aggregates in Cells Exposed to Mitchondrial Inhibitors," *J. Biol. Chem.*, 277(7):5411-5417 (2002).

Lee et al., "Human α-synuclein-harboring familial Parkinson's disease-linked Ala-53→Thr mutation causes neorodegenerative disease with α-synuclein aggregation in transgenic mice," *PNAS*, 99:8968-8973 (2002).

Lee et al., "Truncated alpha-synuclein is generate in vivo and potentiates alpha synuclein aggregation," Database Biosis [Online] Biosciences Information Service, Philadelphia, PA, US (2003), Abstract only.

Lemere, C. A. et al., Amyloid-Beta Immunization in Alzheimer's Disease Transgenic Mouse Models and Wildtype Mice, *Neurochem Res.*, 28(7):1017-27.2003).

Lemere, et al., "Nasal Aβ treatment induces anti-Aβ antibody production and decreases cerebral amyloid burden in PD-APP mice," *Annals of the NY Acad. Sci.*, 920:328-331 (2000).

Lippa et al., "Antibodies to α-Synuclein Detect Lewy Bodies in Many Down's Syndrome Brains with Alzheimer's Disease," *Ann. Neurol.*, 45:353-357 (1999).

Lippa et al., "Alpha-Synuclein in Familial Alzheimer Disease: Epitope Mapping Parallels Dementia With Lewy Bodies and Parkinson Disease," Archives of Neurology, 58(11):1817-1820 (2001).

Lucking et al., "Alpha-synuclein and Parkinson's disease," *Cell. Mol. Life Sci.*, 57:1894-1908 (2000).

Luthi-Carter, R., "Progress towards a Vaccine for Huntington's Disease," *Mol Ther,*. 7(5, Pt 1):569-70 (2003).

Ma et al., "A-synuclein aggregation and neurodegenerative diseases," *Journal of Alzheimer's Disease*, 5(2):139-148 (2003).

Masliah et al., "Dopaminergic Loss and Inclusion Body Formation in α-Synuclein Mice: Implications for Neurodegenerative Disorders," *Science*, 287:1265-1268 (2000).

Masliah et al., "Effects of α-Synuclein Immunization in a Mouse Model of Parkinson's Disease," *Neuron*, 46: 857-868 (2005).

Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).

McLean, et al., "Membrane Association and Protein Conformation of Alpha-Synuclein in Intact Neurons," *J Biol Chem.*, 275(12):8812-6 (2000).

Merriam-Webster online medical dictionary, entry for "cure", accessed Sep. 5, 2006.

Mishizen-Eberz et al., "Distinct cleavage patterns of normal and pathologic forms of α-synuclein by calpain I in vitro," *J. Neurochemistry*, 86:836-847 (2003).

Morgan, et al., "Aβ peptide vaccination prevents memory loss in an animal model of Alzheimer's disease," *Nature*, 408(6815):982-5 (2000).

Munch et al., "Potentiall neurotoxic inflammatory response to Aβ vaccination in humans," *J. Neural Transm.*, 109:1081-1087 (2002).).

NCBI database search result for P37840 Alpha-synuclein conducted Oct. 21, 2002 at http://www.ncbi.nlm.nih.gov/entrez/query.fcgi?cmd=Retrieve&DB=protein&list_uids=58.

NCBI database search result for NP_009292 synuclein, alpha conducted Oct. 21, 2002 at http://www.ncbi.nlm.nih.gov/entrez/query.fcgi?cmd=Retrieve&db=protein&list_uids=68.

Okochi, M. "Constitutive Phosphorylation of the Parkinson's Disease Associated α-Synculein," *J. Biol. Chem.*, 275(1): 390-397 (2000).

Palha et al., "Antibody recognition of amyloidogenic transthyretin variants in serum of patients with familial amyloidiotic polyneuropathy," *J. Mol. Med.*, 78(703-707 (2001).

PCT Search report of Apr. 7, 2009 for application PCT/US08/02392.

PCT/US05/37875 International Preliminary Report on Patentability Chapter 1 issued Apr. 24, 2007 with Written Opinion.

PCT/US05/28166 International Preliminary Report on Patentability Chapter 1 issued Feb. 13, 2007 with Written Opinion.

PCT/US04/37444 International Preliminary Report on Patentability Chapter 1 issued Jun. 19, 2007 with Written Opinion.

PCT/US04/015836 International Preliminary Report on Patentability Chapter 1 issued Nov. 25, 2005 with Written Opinion.

PCT/US00/015239 International Preliminary Examination Report dated Aug. 13, 2001.

Perutz et al., "Amyloid fibers are water-filed nanotubes," *PNAS*, 99(8):5591-5595 (2002).

Perrin et al., "Epitope mapping and specificity of the anti-α-synuclein monoclonal antibody Syn-1 in mouse brain and cultured cell lines," *Neuroscience Letters*, 349:133-135 (2003), abstract only.

Primavera et al., "Brain Accumulation of Amyloid-β in Non-Alzheimer Neurodegeneration," *Journal of Alzheimer's Disease*, 1:183-193 (1999).

Que et al., "Effect of Carrier Selection on Immunogenicity of Protein Conjugate Vaccines against Plasmodium falciparum Circumsporozoites," *Infection and Immunity*, 56(10): 2645-2649 (1988).

Raso, "Immunotherapy of Alzheimer's Disease," *Immunotherapy Weekly*, Abstract (Apr. 2, 1998).

Rochet et al., "Inhibition of fibrillization and accumulation of prefibrillar oligomers in mixtures of human and mouse α-synuclein" *Biochemistry*, 39(35):10619-10626 (2000).

Schenk, D., "Amyloid-β immunotherapy for Alzheimer's disease: the end of the beginning," *Nature Reviews*, 3:824-828 (2002).

Schenk et al., "Immunization with amyloid-β attenuates Alzheimer-disease-like pathology in the PDAPP mouse," *Nature*, 400:173-177 (1999).

Sidhu et al., "Does α-synuclein modulate dopaminergic synaptic content and tone at the synapse," *FASEB*, 18:637-647 (2004).

Sigurdsson et al., "Immunization Delays the Onset of Prion Disease in Mice," *American Journal of Pathology*, 161:13-17 (2002).

Spillantini et al., "α-Synuclein in Lewy bodies," Nature, 388:839-840 (1997).

Sigurdsson et al., "Anti-prion antibodies for prophylaxis following prion exposure in mice," *Neuroscience Letters*, 336:185-187 (2003).

SIPE, "Amyloidosis," *Annu. Rev. Biochem.*, 61:947-975 (1992).

Skipper et al., "Parkinson's Genetics: molecular Insights for the New Millennium," *Neurotoxicology*, 23: 503-514 (2002).

Skolnick and Fetrow, "From genes to protein structure and function: novel applications of computational approaches in the genomic era," *Trends in Biotech*, 18(1):34-39 (2000).

Small et al., "Alzheimer's disease and Abeta toxicity: from top to bottom," *Nat Rev Neurosci.*, 2(8):595-598 (2001).

Small et al., "Cerebral metabolic and cognitive decline in persons at genetic risk for Alzheimer's disease," *PNAS*, 97(11):6037-6042 (2000).

Solomon et al., "Monoclonal antibodies inhibit in vitro fibrillar aggregation of the Alzheimer β-amyloid peptide," *PNAS*, 93:452-455 (1996).

Solomon B., "Immunological approaches as therapy for Alzheimer's disease," *Expert Opin. Biol. Ther.*, 2(8):907-917 (2002).

St. George-Hyslop et al., "Antibody clears senile plaques," *Nature*, 400:116-117 (1999).

Stein et al., "Lack of Neurodegeneration in Transgenic Mice Overexpressing Mutant Amyloid Precursor Protein Is Associated with Increased Levels of Transthyretin and Activation of Cell Survival Pathways," *The Journal of Neuroscience*, 22(17):7380-7388 (2002).

Su et al., "Intravascular infusions of soluble β-amyloid compromise the blood-brain barrier, activate CNS Glial cells and induce peripheral hemorrhage," *Brain Research*, 818:105-107 (1999).

Takahashi, M. "Phosphorylation of α-synuclein characteristic of synculeinopathy lesions is recapitulated in α-synuclein transgenic Drosophila," *Neuroscience Letters*, 336: 155-158 (2003).

Takeda et al., "Abnormal Accumulation of NACP/α-Synuclein in Neurodegenerative Disorders," American Journal of Pathology, 152:367-372 (1998).

Takeda et al., "Abnormal Distribution of the Non-Aβ Component of Alzheimer's Disease Amyloid Precursor/alpha-synuclein in Lewy Body Disease as Revealed by Proteinase K and Fromic Acid Pretreatment," *Laboratory Investigation*, 79(9):1169-1177 (1998).

Takeda, A. et al., "C-terminal alpha-synuclein immunoreactivity in structures other than Lewy bodies in neurodegenerative disorders," *Acta Neuropathol*, 99:296-304 (2000).

Tal et al., "Complete Freund's Adjuvant Immunization Prolongs Survival in Experimental Prion Disease in Mice," *Journal of Neuroscience Research*, 71:286-290 (2003).

Tanaka et al., "NC-1900, an active fragment analog of arginine vasopressin, improves learning and memory deficits induced by beta-amyloid protein in rats," *European J. Pharmacology*, 352:135-142 (1998).

Tennent et al., "Serum amyloid P component prevents proteolysis of the amyloid fibrils of Alzheimer's disease and systemic amyloidosis," *PNAS*, 92:4299-4303 (1995).

Tofaris et al., "Physiological and Pathological Properties of α-synuclein," Cellular and Molecular Life Sciences, pp. 1-8 (2007).

Tofaris et al., "Ubiquitination of alpha-synuclein in Lewy bodies in a pathological event not associated with impairment of proteasome function," The Journal of Biological Chemistry, 278: 44405-44411 (2003).

Tsim, K.W. et al., "Monoclonal antibodies specific for the different subunits of asymmetric acetylcholinesterase from chick muscle," *J. Neurochem.*, 51(1):95-104 (1988).

Ubol et al., "Roles of Immunoglobulin Valency and the Heavy-Chain Constant Domain in Antibody-Mediated Downregulation of Sindbis Virus Replication in Persistently Infected Neurons," *J Virol.*, Mar. 1995; 69(3): 1990-1993

Ueda et al., "Molecular cloning of cDNA encoding an unrecognized component of amyloid in Alzheimer disease," *PNAS*, 90:11282-11286 (1993).

Vickers, J.C., "A vaccine against Alzheimer's disease, Developments to date," *Drugs Aging*, 19(7): 487-494 (2002).

Wakabayashi et al., "α-Synuclein immunoreactivity in glial cytoplasmic inclusions in multiple system atrophy," *Neuroscience Letters*, 249:180-182 (1998).

Wakabayashi et al., "NACP, a presynaptic protein, immunoreactivity in Lewy bodies in Parkinson's disease," *Neuroscience Letters*, 239(1) 45-48 (1997).

Wakabayashi et al., "Widespread occurrence of a-synuclein/NCAP-immunoreactive neuronal inclusions in juvenile and adult-onset Hallervorden-Spatz disease with Lewy bodies," *Neuropathology and Applied Neurobiology*, 25(5): 363-368 (1999).

Wakabayashi et al., "Accumulation of a-synuclein/NACP is a cytopathological feature common to Lewy body disease and multiple system atrophy," *Acta Neuropathol.*, 96(5): 445-452 (1998).

Walker et al., "Labeling of Cerebral Amyloid In Vivo with a Monoclonal Antibody," *J. Neuropath. Exp. Neurology*, 53(4):377-383 (1994).

Wanker, "Protein aggregation in Huntington's and Parkinson's disease: Implications or therapy," Molecular Medicine Today 2000 GB, 6(10):387-397 (2000), Abstract only.

Watson et al., "Chapter 14: The Introduction of Foreign Genes into Mice," *Molecular Biology of Watson Recombinant DNAs, 2nd ed.*, 255-272 (1993).

Weinreb et al., "NACP, A Protein Implicated in Alzheimer's Disease and Learning, Is Natively Unfolded," *Biochemistry*, 35(43):13709-13715 (1996).

Windisch et al., "Development of a new treatment for Alzheimer's disease and Parkinson's disease using anti-aggregatory [beta]-synuclein-derived peptides," Journal of Molecular Neuroscience, 19(2): 63-69 (2002) abstract only.

Wisniewski et al., "Therapeutics in Alzheimer's and Prion Diseases," *Biochemical Society Transactions*, 30(4):574-587 (2002).

Wong et al., "Neuritic Plaques and Cerebrovascular Amyloid in Alzheimer Disease are Antigenically Related," *PNAS*, 82:8729-8732 (1985).

Yoshimoto et al., "NACP, the precursor protein of the non-amyloid β/A4 protein (Aβ) component of Alzheimer disease amyloid, binds Aβ and stimulates Aβ aggregation," *PNAS*, 92:9141-9145 (1995).

Younkin, "Amyloid β vaccination: reduced plaques and improved cognition," *Nature Medicine*, 7(1):18-19 (2001).

Zhou et al., "A Human Single-Chain Fv Intrabody Blocks Aberrant Cellular Effects of Overexpressed alpha-Synuclein," *Mol Ther.*, 10(6):1023-1031 (2004).

* cited by examiner

US 7,910,333 B2

ANTIBODIES TO ALPHA-SYNUCLEIN

CROSS-REFERENCE TO RELATED APPLICATION

The present application is a continuation application of U.S. application Ser. No. 10/984,192; filed Nov. 8, 2004, which claims the benefit of U.S. Provisional Application No. 60/518,140; filed Nov. 8, 2003, the disclosures of both of which are incorporated by reference in their entirety for all purposes.

BACKGROUND OF THE INVENTION

Alpha-synuclein (alphaSN) brain pathology is a conspicuous feature of several neurodegenerative diseases, including Parkinson's disease (PD), dementia with Lewy bodies (DLB), the Lewy body variant of Alzheimer's disease (LB-VAD), multiple systems atrophy (MSA), and neurodegeneration with brain iron accumulation type-1 (NBIA-1). Common to all of these diseases, termed synucleinopathies, are proteinaceous insoluble inclusions in the neurons and the glia which are composed primarily of alphaSN.

Lewy bodies and Lewy neurites are intraneuronal inclusions which primarily contain of alphaSN. Lewy bodies and Lewy neurites are the neuropathological hallmarks Parkinson's disease (PD). PD and other synucleinopathic diseases have been collectively referred to as Lewy body disease (LBD). LBD is characterized by degeneration of the dopaminergic system, motor alterations, cognitive impairment, and formation of Lewy bodies (LBs). (McKeith et al., *Clinical and pathological diagnosis of dementia with Lewy bodies (DLB): Report of the CDLB International Workshop, Neurology* (1996) 47:1113-24). Other LBDs include diffuse Lewy body disease (DLBD), Lewy body variant of Alzheimer's disease (LBVAD), combined PD and Alzheimer's disease (AD), and multiple systems atrophy. Dementia with Lewy bodies (DLB) is a term coined to reconcile differences in the terminology of LBDs.

Disorders with LBs continue to be a common cause for movement disorders and cognitive deterioration in the aging population (Galasko et al., *Arch. Neurol.* (1994) 51:888-95). Although their incidence continues to increase creating a serious public health problem, to date these disorders are neither curable nor preventable and understanding the causes and pathogenesis of PD is critical towards developing new treatments (Tanner et al., *Curr. Opin. Neurol.* (2000) 13:427-30). The cause for PD is controversial and multiple factors have been proposed to play a role, including various neurotoxins and genetic susceptibility factors.

In recent years, new hope for understanding the pathogenesis of PD has emerged. Specifically, several studies have shown that the synaptic protein alpha-SN plays a central role in PD pathogenesis since: (1) this protein accumulates in LBs (Spillantini et al., *Nature* (1997) 388:839-40; Takeda et al., *AM. J. Pathol.* (1998) 152:367-72; Wakabayashi et al., *Neurosci. Lett.* (1997) 239:45-8), (2) mutations in the alpha-SN gene co-segregate with rare familial forms of parkinsonism (Kruger et al., *Nature Gen.* (1998) 18:106-8; Polymeropoulos M H, et al., *Science* (1997) 276:2045-7) and, (3) its overexpression in transgenic mice (Masliah et al., *Science* (2000) 287:1265-9) and *Drosophila* (Feany et al., *Nature* (2000) 404:394-8) mimics several pathological aspects of PD. Thus, the fact that accumulation of alpha-SN in the brain is associated with similar morphological and neurological alterations in species as diverse as humans, mice, and flies suggests that this molecule contributes to the development of PD.

Alpha-SN is part of a large family of proteins including beta- and gamma-synuclein and synoretin. Alpha-SN is expressed in the normal state associated with synapses and is believed to play a role in neural plasticity, learning and memory. Mutations in human (h) alpha-SN that enhance the aggregation of alpha-SN have been identified (Ala30Pro and Ala53Thr) and are associated with rare forms of autosomal dominant forms of PD. The mechanism by which these mutations increase the propensity of alpha-SN to aggregate are unknown.

SUMMARY OF THE CLAIMED INVENTION

The invention provides a monoclonal antibody that competes with a monoclonal antibody shown in Table 1 for specific binding to alpha synuclein. Optionally, the monoclonal antibody specifically binds alpha synuclein compared to beta synuclein. Optionally, the monoclonal antibody specifically binds human alpha synuclein compared to non-human alpha synuclein. Optionally, the monoclonal specifically binds to an epitope bound by a monoclonal antibody shown in Table 1. Some antibodies specifically binds to an epitope within residues 109-120, or to an epitope on the C-terminus of synuclein, or to an epitope comprising residues 139-140. Some antibodies specifically bind to an epitope on the N-terminus of synuclein. Some antibodies specifically bind to an epitope within residues 43-51 and within residues 58-65. Some antibodies specifically bind to a repeated epitope comprising residues within residues 43-51 and residues within residues 58-65. Some antibodies specifically bind to an epitope within residues 118-126. Some antibodies specifically bind to an epitope comprising residues 91-99. Some antibodies specifically bind to an epitope comprising residues 40-55. Some antibodies specifically bind to an epitope comprising residues 124-134, wherein residue 129 is phosphorylated serine. Some antibodies specifically bind to an epitope comprising residues 123-127, wherein residue 125 is nitrated tyrosine. Some antibodies specifically binds to human alpha synuclein without specifically binding to mouse alpha synuclein.

Preferred antibodies include 9E4 or an antibody that competes with 9E4 for specific binding to human alpha synuclein. Other preferred antibodies include 11A5 or an antibody that competes with 11A5 for specific binding to phosphorylated human alpha synuclein. Other preferred antibodies include 6H7 or an antibody that competes with 6H7 for specific binding to alpha synuclein. Other preferred antibodies include 4B1 or 8A5 or an antibody that competes with 4B1 or 8A5 for specific binding to alpha synuclein. Other preferred antibodies include 7G4, 6A8, 5C12, 6A12, 9G5, and 1H7, and antibodies that competes therewith for specific binding to alpha synuclein.

Some antibodies specifically bind to mouse alpha synuclein without specifically binding to human alpha synuclein. Some antibodies specifically bind to mouse and human alpha synuclein. Some antibodies specifically bind to alpha synuclein phosphorylated at residue 129 without specifically binding to nonphosphorylated alpha synuclein. Some antibodies are end-specific for the N-terminus or C-terminus of alpha synuclein. Some antibodies specifically bind to alpha synuclein without specifically binding to beta or gamma synuclein.

Some antibodies specifically bind to an epitope within a segment of amino acids selected of the group consisting of amino acids 109-120, 43-51 and 58-65, 91-96, 118-126, and 91-99. Exemplary monoclonal antibodies are shown in Table 1 and include 7G4, 6A8, 5C12, 6A12, 8A5, 4B1, 6H7, 3A12, 12C1, 9A6, 9G5, 9E4, 23E8, 10G5, 3C12, 11A5 and 1H7.

Some antibodies are monoclonal antibodies that specifically binds to phosphorylated alpha synuclein. Some antibodies are monoclonal antibodies that specifically bind to nitrated synuclein. Some antibodies are monoclonal antibodies capable of capturing soluble synuclein from a fluid sample, preferably alpha-synuclein and more preferably human alpha synuclein.

Some antibodies are monoclonal antibodies that specifically bind to an epitope within residues selected from the group consisting of the N-terminus, 118-126, 91-99 and 40-55. Some monoclonal antibodies competes with the monoclonal antibody selected from the group consisting of 6H7, 3QA12, 12C6, 12C1, 9A6, 9G5, 9E4, 1H7 and 23E8. Exemplary antibodies include monoclonals 6H7, 3QA12, 12C6. 12C1, 9A6, 9G5, 9E4, 1H7 and 23E8.

The invention further provides a pair of monoclonal antibodies, each of the monoclonal antibodies specifically binding to a different epitope within synuclein, wherein the monoclonal antibodies are capable of detecting soluble synuclein when used together in an ELISA assay. Optionally, one monoclonal antibody is immobilized to a solid phase. In some methods, the use of the monoclonal antibodies in the ELISA assay is sequential. In some methods, one monoclonal antibody is a capture antibody and the other monoclonal antibody is a reporter antibody. In some methods, the capture antibody specifically binds an epitope within residues selected from the group consisting of N-terminus, 40-55, 91-99 and 118-126, and the reporter antibody specifically binds an epitope within residues 109-120. In some methods, the pair is selected from the group of an antibody that competes with 6H7 and an antibody that competes with 5C12 or 12C1, an antibody that competes with 3A12 and an antibody that competes with 5C12 or 6H7, an antibody that competes with 12C1 and an antibody that competes with 5C12 or 6H7, an antibody that competes with 9A6 and an antibody that competes with 5C12, 6H7 or 12C1, an antibody that competes with 9G5 and an antibody that competes with 5C12, 6H7 or 12C1, an antibody that competes with 9E4 and an antibody that competes with 5C12, 6H7 or 12C1, an antibody that competes with 1H7 and an antibody that competes with 5C12, 6H7 or 12C1, and an antibody that competes with 10G5 and an antibody that competes with 5C12, 6H7 or 12C1. Optionally, the pair is selected from the group of 6H7 and 5C12 or 12C1; 3A12 and 5C12 or 6H7; 12C1 and 5C12 or 6H7; 9A6 and 5C12, 6H7 or 12C1; 9G5 and 5C12, 6H7 or 12C1; 9E4 and 5C12, 6H7 or 12C1; 1H7 and 5C12, 6H7 or 12C1; and 10G5 and 5C12, 6H7 or 12C1.

The invention further provides a hybridoma producing a monoclonal antibody shown in Table 1.

The invention further provides a humanized or chimeric version of a monoclonal antibody shown in Table 1.

The invention further provides a method of humanizing a monoclonal antibody shown in Table 1, comprising: determining the amino acid sequence of CDR regions of the monoclonal antibody; selecting an acceptor antibody; and producing a humanized antibody comprising the CDRs from the monoclonal antibody and variable region frameworks from the acceptor antibody.

The invention further provides a method of producing a chimeric form of an antibody shown in Table 1, comprising: determining the amino acid sequence of the light and heavy chain variable regions of the monoclonal antibody; selecting heavy and light chain constant region; producing a chimeric antibody comprising a light chain comprising the light chain variable region fused to the light chain constant region, and a heavy chain comprising the heavy chain variable region fused to the heavy chain constant region.

The invention further provides a method for detecting alpha synuclein in a fluid sample, comprising capturing the alpha synuclein using a capture antibody and detecting the alpha synuclein using a reporter antibody, wherein the capture and reporter antibodies bind to different epitopes on alpha synuclein. In some methods, the fluid sample contains 0.1-1.0 M guanidine. In some methods, the fluid sample contains 0.5 M guanidine. In some methods, the reporter antibody or the capture antibody is end-specific for the C-terminal end of SN1-119 or SN1-122. In some methods, the capturing step is performed twice with a first reporter antibody specifically binding to an epitope within SN1-119 and a second reporter antibody specifically binding to an antibody within SN120-140 and determining a ratio of captured alpha synuclein between the two steps, a higher ratio of synuclein captured by first reporter relative to second report being indicative of pathogenicity. In some methods, the reporter antibody in the first capturing step specifically binds to an epitope within SN 109-120, and the reporter antibody in the second capturing step specifically binds to an epitope within SN 120-126, and the capture antibody in both capturing steps specifically binds to an epitope within SN 91-99. In some methods, the capture antibody is immobilized to a solid phase, and the reporter antibody in solution, and the detecting step comprises detecting alpha synuclein from presence of the reporter antibody linked to the solid phase via binding of the reporter antibody to alpha synuclein, which is in turn bound to the capture antibody. Some methods involve a further step of comparing a signal from the reporter antibody linked to the solid phase from analyzing the sample with a signal from the reporter antibody linked to the solid phase from analyzing a control sample containing a known amount of alpha synuclein to determine the amount of alpha synuclein in the sample. In some methods, a signal from the reporter antibody linked to the solid phase from analyzing the sample to a calibration curve of signal is compared with an amount of alpha synuclein to determine the amount of alpha synuclein in the sample. In some methods, a signal from the reporter antibody is proportional to the amount of synuclein in the sample. Some methods further comprise contacting the reporter antibody with a labeled antibody to generate a signal indicating presence of the reporter antibody. In some methods, the capture antibody specifically binds to an epitope within amino acids 91-99 of human alpha synuclein and the reporter antibody binds to an epitope within amino acids 109-120 of alpha synuclein. In some methods, the capture antibody is 1H7 and the reporter antibody is 5C12. In some methods, the sample is a sample from a human. In some methods, the capture antibody is 1H7 and the reporter antibody is 9E4. In some methods, the sample from a mouse. In some methods, the sample is a body fluid. In some methods, the sample is cerebrospinal fluid (CSF) of a human. In some methods, the sample is a brain homogenate of a human or transgenic animal. In some methods, the sample is a medium used to culture cells. In some methods, the cells express recombinant alpha synuclein. In some methods, the sample contains a fragment of full-length alpha synuclein and the detecting step detects the fragment.

The invention further provides a method of monitoring processing of alpha-synuclein to a fragment, comprising culturing a cell expressing alpha synuclein and processing the alpha synuclein to a fragment that is secreted to the cell media; and detecting the fragment in the cell media. In some methods, the cell is a Peak5 or SY5Y cell transfected with alpha synuclein. In some methods, the cell is a cortical cell.

The invention further provides a method of screening an agent for activity in inhibiting processing or secretion of alpha synuclein, comprising contacting a cell expressing alpha synuclein in culture medium with an agent; detecting alpha synuclein or a fragment thereof in the medium; and comparing the amount of alpha synuclein or the fragment in the medium with an among of alpha synuclein or fragment in medium from a control cell not contacted with the agent, wherein a reduction in the amount of alpha synuclein or the fragment indicates the agent inhibits processing or secretion of the alpha synuclein.

The invention further provides a method for detecting soluble alpha synuclein in a fluid sample, comprising: capturing the soluble fragment from the sample using a first binding substance under conditions in which the first binding substance specifically binds to a first epitope and detecting capture of the soluble alpha synuclein using a second binding substance which binds to an epitope on a second region of the soluble alpha synuclein different from the first epitope.

The invention further provides a method for detecting a soluble fragment of alpha synuclein in a fluid sample in the presence of full length alpha synuclein the method comprising: capturing the soluble fragment from the sample using a first binding substance, and detecting the soluble fragment using a second binding substance, wherein both binding substances specifically bind to the fragment and at least one specifically binds to the fragment without binding to full length alpha synuclein.

DEFINITIONS

Figure 1A:
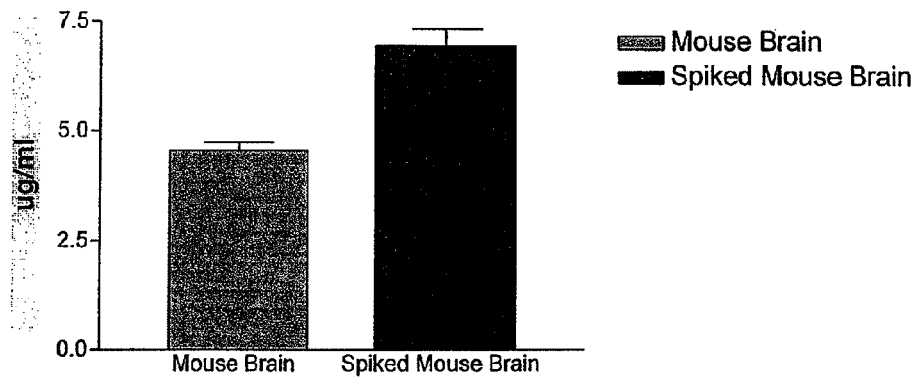
FIGS. 1A and B show quantitative detection of alpha synuclein using an ELISA assay with two pairs of antibodies 1H7/5C12 and 1H7/9E4 respectively.

The phrase that an antibody "specifically binds" to a target refers to a binding reaction which is determinative of the presence of the antibody in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$ $M^{-1}$, or $10^{10}$ $M^{-1}$. Affinities greater than $10^8$ $M^{-1}$ are preferred. Lack of specific binding means an affinity of less than $10^6 M^{-1}$.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., J. Immunol. 148, 1547-1553 (1992).

Antibodies of the invention are typically substantially pure from undesired contaminant. This means that an agent is typically at least about 50% w/w (weight/weight) purity, as well as being substantially free from interfering proteins and contaminants. Sometimes the antibodies are at least about 80% w/w and, more preferably at least 90 or about 95% w/w purity. However, using conventional protein purification techniques, homogeneous peptides of at least 99% w/w can be obtained.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen.

The term "compete" means competition between antibodies is determined by an assay in which the immunoglobulin under test inhibits specific binding of a reference antibody to a common antigen, such as alpha-SN. Numerous types of competitive binding assays are known, for example: solid phase direct or indirect radioimmunoassay (RIA), solid phase direct or indirect enzyme immunoassay (ETA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, *Antibodies, A Laboratory Manual*, Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

The terms "conditioned culture medium" and "culture medium" refer to the aqueous extracellular fluid which surrounds cells grown in tissue culture (in vitro) and which contains, among other constituents, proteins and peptides secreted by the cells.

The term "body fluid" refers to those fluids of a mammalian host which is suspected contain measurable amounts of alpha synuclein or fragments thereof, specifically including blood, cerebrospinal fluid (CSF), urine, and peritoneal fluid. The term "blood" refers to whole blood, as well as blood plasma and serum.

A "pharmacological" activity means that an agent at least exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

An end-specific antibody means an antibody whose epitope includes a terminal residue of an antigen, and the antibody specifically binds to the antigen only when that residue has a free end. For example, an antibody that binds to the N-terminus of alpha synuclein when the alpha synuclein is not linked to any other protein but which does not specifically bind when the N-terminus of alpha synuclein is fused to another protein is an end-specific antibody.

A synucleinopathic disease means a disease characterized by Lewy bodies, Lewy neurites or other deposits of alpha synuclein.

An immunogenic fragment of alpha synuclein is one capable of inducing a humoral (antibody mediated) and/or a cellular (mediated by antigen-specific T cells or their secretion products) when administered to a subject.

Compositions or methods "comprising" one or more recited elements may include other elements not specifically recited. For example, a composition that comprises alpha-SN peptide encompasses both an isolated alpha-SN peptide and alpha-SN peptide as a component of a larger polypeptide sequence.

DETAILED DESCRIPTION

I. Antibodies of the Invention

The invention provides several exemplary monoclonal antibodies to different epitopes of alpha synuclein as shown in Table 1. Hybridomas producing the respective antibodies are also provided. The hybridomas producing the antibodies have been deposited with the American Type Culture Collection (ATCC) at 10801 University Boulevard, Manassas, Va. 20110-2209. The cell line designated JH22.11A5.6.29.70.54.16.14, producing the antibody 11A5 having the ATCC accession number PTA-8222 has been deposited on Feb. 26, 2007 at the ATCC; the cell line designated JH4.8A5.25.7.36, producing the antibody 8A5 having the ATCC accession number PTA-6909 has been deposited on Aug. 4, 2005 at the ATCC; the cell line designated JH17.1H7.4.24.34, producing the antibody 1H7 having the ATCC accession number PTA-8220, has been deposited on Feb. 26, 2007 at the ATCC; the cell line designated JH17.9E4.3.37.1.14.2, producing the antibody 9E4 having the ATCC accession number PTA-8221 has been deposited on Feb. 26, 2007 at the ATCC; the cell line designated JH17.6H7.1.54.28, producing the antibody 6H7 having the ATCC accession number PTA-6910 has been deposited at the ATCC; the cell line designated JH4.5C12.4.15.57, producing the antibody 5C12 having the ATCC accession number PTA-9197 has been deposited on May 8, 2008 at the ATCC. The first column of Table 1 shows the name of an antibody. The same name is used to refer to an antibody and the hybridoma producing it. The second column shows the antigen used to generate the antibody. The third column indicates the epitope bound by the antibody. The fourth column indicates the isotype. The fifth column indicates applications of the antibody (immunofluorescence, Western blot, immunoprecipitation, histology, and capture and reporter antibody for a sandwich assay). The invention further provides humanized and chimeric forms of mouse monoclonals, particularly of the exemplified antibodies shown in Table 1.

The invention also provides other antibodies that compete with one of the exemplified antibodies for specific binding to alpha-synuclein (i.e., bind to the same epitope as an exemplified antibody or a sufficiently proximal epitope to interfere with the binding of an exemplified antibody to its epitope). The invention also provides antibodies that bind to the same epitope as one of the exemplified antibodies. Antibodies that compete with or bind to the same epitope as an exemplified antibody are expected to show similar functional properties. Such antibodies include mouse and other nonhuman antibodies, human antibodies, chimerics and humanized antibodies. Such antibodies include monoclonal antibodies and polyclonal antibody. A polyclonal antibody specifically binds to an epitope if it binds to the epitope without binding to other regions of alpha synuclein. This is usually true of a monoclonal antibody as well. However, some monoclonal antibodies can be designed or selected to have specificity for two epitopes within alpha synuclein.

Some preferred epitope specificities include monoclonal antibodies that specifically binds to a repeated epitope comprising residues within residues 43-51 and residues within residues 58-65, monoclonal antibodies that specifically binds to an epitope within residues 118-126; monoclonal antibodies that specifically binds to an epitope comprising residues 91-99, monoclonal antibodies that specifically binds to an epitope comprising residues 40-55; monoclonal antibodies that specifically binds to an epitope comprising residues 124-134, wherein residue 129 is phosphorylated serine, and monoclonal antibodies that specifically binds to an epitope comprising residues 123-127, wherein residue 125 is nitrated tyrosine.

When an antibody is said to bind to an epitope within specified residues, such as alpha-SN 109-120, for example, what is meant is that the antibody specifically binds to a polypeptide consisting of the specified residues (i.e., alpha-SN 109-120 in this an example). Such an antibody does not necessarily contact every residue within alpha-SN 109-120. Nor does every single amino acid substitution or deletion within alpha-SN109-120 necessarily significantly affect binding affinity. Epitope specificity of an antibody can be determined, for example, by testing a collection of overlapping peptides of about 15 amino acids spanning the sequence of alpha-synuclein and differing in increments of a small number of amino acids (e.g., 3 amino acids). The peptides are immobilized within the wells of a microtiter dish. Immobilization can be effected by biotinylating one terminus of the peptides. Optionally, different samples of the same peptide can be biotinylated at the N and C terminus and immobilized in separate wells for purposes of comparison. Such is particularly useful for identifying end-specific antibodies. Optionally, additional peptides can be included terminating at a particular amino acid of interest (e.g., the first and last residue of the NAC fragment). Such is particularly useful for identifying end-specific antibodies to internal fragments of alpha synuclein. An antibody is screened for specific binding to each of the various peptides. The epitope is defined as occurring within a segment of amino acids that is common to all peptides to which the antibody shows specific binding.

i. General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology*, Paul, W., ed., 2nd ed. Raven Press, N.Y., 1989, Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991); Chothia & Lesk, *J. Mol. Biol.* 196:901-917 (1987); or Chothia et al., *Nature* 342:878-883 (1989).

ii. Production of Nonhuman Antibodies

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, DNA encoding the variable domains of a mouse antibody can be sequenced, and DNA construct(s) encoding the variable domains joined to human constant (C) segments, such as IgG1 and IgG4 constructed. The constructs are then expressed to produce the antibody Human isotype IgG1 is preferred. In some methods, the isotype of the antibody is human IgG1. IgM antibodies can also be used in some methods. A typical chimeric antibody is thus a hybrid protein consisting of the V or antigen-binding domain from a mouse antibody and the C or effector domain from a human antibody.

Humanized antibodies have variable region framework residues substantially from a human antibody or consensus of human antibodies (termed an acceptor antibody) and some and usually all six complementarity determining regions substantially or entirely from a mouse-antibody, (referred to as the donor immunoglobulin). See, Queen et al., *Proc. Natl. Acad. Sci. USA* 86:10029-10033 (1989), WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539 (each of which is incorporated by reference in its entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 A of a CDR region), or
(4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

iii. Human Antibodies

Human antibodies against alpha-SN are provided by a variety of techniques described below. Some human antibodies are selected by competitive binding experiments, or otherwise, to have the same epitope specificity as a particular mouse antibody, such as one of the mouse monoclonals shown in Table 1. Human antibodies can also be screened for a particular epitope specificity by using only a fragment of alpha-SN as the immunogen, and/or by screening antibodies against a collection of deletion mutants of alpha-SN. Human antibodies preferably have isotype specificity human IgG1. Several methods are available for producing human antibodies including the trioma method, Oestberg et al., *Hybridoma* 2:361-367 (1983); Oestberg, U.S. Pat. No. 4,634,664; and Engleman et al., U.S. Pat. No. 4,634,666 (each of which is incorporated by reference in its entirety for all purposes); transgenic non-human mammals described in detail by, e.g., Lonberg et al., WO93/1222, U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (each of which is incorporated by reference in its entirety for all purposes); and phage display methods See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes).

iv. Selection of Constant Region

The heavy and light chain variable regions of chimeric, humanized, or human antibodies can be linked to at least a portion of a human constant region. The choice of constant region depends, in part, whether antibody-dependent complement and/or cellular mediated toxicity is desired. For example, isotopes IgG1 and IgG3 have complement activity and isotypes IgG2 and IgG4 do not. Choice of isotype can also affect passage of antibody into the brain. Human isotype IgG1 is preferred. Light chain constant regions can be lambda or kappa. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

v. Expression of Recombinant Antibodies

Chimeric, humanized and human antibodies are typically produced by recombinant expression. Recombinant polynucleotide constructs typically include an expression control sequence operably linked to the coding sequences of antibody chains, including naturally associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines, various COS cell lines, HeLa cells, L cells, human embryonic kidney cell, and myeloma cell lines. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. No. 5,741,957, U.S. Pat. No. 5,304,489, U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, and gel electrophoresis and the like (see generally, Scopes, Protein Purification (Springer-Verlag, NY, 1982).

II. Alpha Synuclein

Alpha synuclein was originally identified in human brains as the precursor protein of the non-β-amyloid component of (NAC) of AD plaques. (Ueda et al., *Proc. Natl. Acad. Sci. U.S.A.* 90 (23):11282-11286 (1993). Alpha-SN, also termed the precursor of the non-Aβ component of AD amyloid (NACP), is a peptide of 140 amino acids. Alpha-SN has the amino acid sequence:

```
                                            (SEQ ID NO: 1)
MDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQL

GKNEEGAPQEGILEDMPVDPDNEAYEMPSEEGYQDYEPEA
(Uéda et al., Ibid.; GenBank accession number:
P37840).
```

The non-Aβ component of AD amyloid (NAC) is derived from alpha-SN. NAC, a highly hydrophobic domain within alpha synuclein, is a peptide consisting of at least 28 amino acids residues (residues 60-87) (SEQ ID NO: 3) and optionally 35 amino acid residues (residues 61-95) (SEQ ID NO: 2). See FIG. 1. NAC displays a tendency to form a beta-sheet structure (Iwai, et al., *Biochemistry*, 34:10139-10145). Jensen et al. have reported NAC has the amino acid sequence:

```
                                            (SEQ ID NO: 2)
EQVTNVGGAVVTGVTAVAQKTVEGAGSIAAATGFV
   (Jensen et al., Biochem. J. 310 (Pt 1): 91-94
   (1995); GenBank accession number S56746).
```

Uéda et al. have reported NAC has the acid sequence:

```
KEQVTNVGGAVVTGVTAVAQKTVEGAGS    (SEQ ID NO: 3)
(Uéda et al., PNAS USA 90: 11282-11286 (1993).
```

Disaggregated alpha-SN or fragments thereof, including NAC, means monomeric peptide units. Disaggregated alpha-SN or fragments thereof are generally soluble, and are capable of self-aggregating to form soluble oligomers. Oligomers of alpha-SN and fragments thereof are usually soluble and exist predominantly as alpha-helices. Monomeric alpha-SN may be prepared in vitro by dissolving lyophilized peptide in neat DMSO with sonication. The resulting solution is centrifuged to remove any insoluble particulates. Aggregated alpha-SN or fragments thereof, including NAC, means oligomers of alpha-SN or fragments thereof which have associate into insoluble beta-sheet assemblies. Aggregated alpha-SN or fragments thereof, including NAC, means also means fibrillar polymers. Fibrils are usually insoluble. Some antibodies bind either soluble alpha-SN or fragments thereof or aggregated alpha-SN or fragments thereof. Some antibodies bind both soluble and aggregated alpha-SN or fragments thereof.

Unless otherwise indicated, reference to alpha-SN means the natural human amino acid sequence indicated above as well as natural allelic and species variants thereof, including full-length forms and immunogenic fragments thereof, as well as forms having undergone posttranslational modification, such as phosphorylation. Induced variants of alpha-SN or can also be used but are not preferred. Such variants typically differ from naturally occurring peptides at one, two or a few positions, often by virtue of conservative substitutions. Analogs can also unnatural amino acids, but such is not preferred.

Alpha-SN, its fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989). Some forms of alpha-SN peptide are also available commercially, for example, at BACHEM and American Peptide Company, Inc.

Beta synuclein shows 78% sequence similarity with alpha synuclein at the amino acid level. Gamma synuclein shares 60% similarity at the amino acid level with alpha-synuclein (see Biere et al., J. Biol. Chem., Vol. 275, Issue 44, 34574-34579, Nov. 3, 2000, incorporated by reference).

III. Assays for Detecting Alpha Synuclein

Antibodies of the invention can be used to detect alpha synuclein or fragments thereof in a variety of formats including immunoprecipitation, Western blotting, ELISA, radioimmunoassay, competitive and isometric assays. See Harlow & Lane, *Antibodies, A Laboratory Manual* (CSHP NY, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Isometric or sandwich assays are a preferred format (see U.S. Pat. Nos. 4,376,110, 4,486,530, 5,914,241, and 5,965,375). Such assays use one antibody immobilized to a solid phase (capture antibody), and another antibody in solution (reporter antibody). Typically, the reporter antibody is labeled, either directly or via a secondary labeling reagent, such as an anti-idiotypic antibody. The capture and reporter antibodies having different binding specificities so both can bind to alpha-synuclein or a fragment thereof at the same time. Capture and reporter antibodies can be contacted with target antigen in either order or simultaneously. If the capture antibody is contacted first, the assay is referred to as being a forward assay. Conversely, if the reporter antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample that do not become specifically bound to the solid phase When capture and reporter antibodies are bound in separate steps, a wash can be performed after either or both binding steps. After washing, binding is quantified, typically by detecting label linked to the solid phase through binding of labeled reporter. Usually for a given pair of antibodies, a calibration curve is prepared from samples containing known concentrations of target antigen. Concentrations of antigen in samples being tested are then read by interpolation from the calibration curve. Analyte can be measured either from the amount of labeled reporter antibody bound at equilibrium or by kinetic measurements of bound labeled solution antibody at a series of time points before equilibrium is reached. The slope of such a curve is a measure of the concentration of target in a sample. Alternatively, the amount of alpha synuclein in a sample can be determined by comparing the signal of reporter antibody bound to alpha synuclein the sample with the signal from reporter antibody bound to a known amount of alpha synuclein in a control sample.

Competitive assays can also be used. In some methods, target alpha-synuclein in a sample competes with exogenously supplied labeled alpha synuclein for binding to an antibody. The amount of labeled alpha synuclein bound to the antibody is inversely proportional to the amount of target alpha synuclein in the sample. The antibody can be immobilized to facilitate separation of the bound complex from the sample prior to detection (heterogeneous assays) or separation may be unnecessary as practiced in homogeneous assay formats. In other methods, the antibody used as a detection reagent is labeled. When the antibody is labeled, its binding sites compete for binding to the target alpha synuclein in the sample and exogenously supplied form of alpha synuclein immobilized on a solid phase.

Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that described the use of such labels include U.S. Pat. Nos. 3,817,837; 3,850,752; 3,939,350;

3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™. (Amersham Pharmacia Biotech, Piscataway N.J., and the like. Immobilization can be by absorption or by covalent attachment. Optionally, antibodies can be joined to a linker molecule, such as biotin for attachment to a surface.

Solvents used to extract alpha synuclein from tissue samples can decrease the sensitivity of the assay (e.g., 5M guanidine, urea/thiourea/CHAPS, urea/thiourea, 1% SDS, 1% SDS/8M, cell lysis buffer). It is recommended that such solvents be removed or diluted such that they account for less than 1% and preferably less than 0.1% of the buffer used for the assay.

Preferred pairs of monoclonal antibodies for use in isometric assays are as follows. In one combination, the capture antibody specifically binds an epitope within residues selected from the group consisting of N-terminus, 40-55, 91-99 and 118-126, and the reporter antibody specifically binds an epitope within residues 109-120. Another suitable pairing is an antibody that specifically binds to an epitope within residues 124-134 and is specific for the phosphorylated form and another antibody that specifically binds to an epitope within residues 91-99. Other suitable pairings include an antibody that competes with 6H7 and an antibody that competes with 5C12 or 12C1; an antibody that competes with 3A12 and an antibody that competes with 5C12 or 6H7; an antibody that competes with 12C1 and an antibody that competes with 5C12 or 6H7; an antibody that competes with 9A6 and an antibody that competes with 5C12, 6H7 or 12C1; an antibody that competes with 9G5 and an antibody that competes with 5C12, 6H7 or 12C1; an antibody that competes with 9E4 and an antibody that competes with 5C12, 6H7 or 12C1; an antibody that competes with 1H7 and an antibody that competes with 5C12, 6H7 or 12C1; and an antibody that competes with 10G5 and an antibody that competes with 5C12, 6H7 or 12C1, and antibody that competes with 1H7 and an antibody that competes with 11A5. Preferred pairings include 6H7 and 5C12 or 12C1; 3A12 and 5C12 or 6H7; 12C1 and 5C12 or 6H7; 9A6 and 5C12, 6H7 or 12C1; 9G5 and 5C12, 6H7 or 12C1; 9E4 and 5C12, 6H7 or 12C1; 1H7 and 5C12, 6H7 or 12C1; 10G5 and 5C12, 6H7 or 12C1, 1H7 and 11A5.

Some method employ either a capture or a reporter antibody that is end-specific for a fragment of alpha-synuclein, particularly, SN1-119 (i.e., residues 1-119 of SEQ ID NO:1) or SN1-122 (residues 1-122 of SEQ ID NO:1). Applications for detection of these fragments are described below.

IV. Applications

A. Body Fluids

In vivo detection of alpha synuclein in patient samples can be used for diagnosing and monitoring diseases characterized by Lewy bodies or other deposits of alpha synuclein. Synucleinopathic diseases include Parkinson's disease (PD), dementia with Lewy bodies (DLB), the Lewy body variant of Alzheimer's disease (LBVAD), multiple systems atrophy (MSA), neurodegeneration with brain iron accumulation type-1 (NBIA-1), diffuse Lewy body disease (DLBD), and combined PD and Alzheimer's disease (AD). Suitable patient samples include body fluids, such as blood, CSF, urine, and peritoneal fluid. The presence of a synucleinopathic disease is generally associated with significantly altered levels of alpha synuclein or fragments thereof in the fluid (increased or decreased) when compared to the mean values in normal individuals, i.e., individuals not suffering from a synucleinopathic disease. A level is significantly altered if it departs by more than one standard deviation from the mean level in a population of normal individuals.

In addition to initial diagnosis of synucleinopathic disease, condition, the measured concentrations of alpha synuclein and its fragment's can be monitored to follow the progress of the disease, and potentially follow the effectiveness of treatment. Levels of alpha-synuclein and its fragments revert toward the mean in a population of normal individuals if the treatment regime is effective.

B. Cell Culture

In vitro monitoring of alpha synuclein and its fragment in conditioned culture medium from a suitable cell culture can be used for analyzing processing and secretion of alpha-synuclein and the effect of potential agents on the same. Monitoring processing of alpha synuclein provides a means to study proteolytic cleavage, identify responsible proteases, determine what factors affect cleavage, and determine the physiological function of truncated forms of alpha synuclein. Agents that inhibit processing and/or secretion of alpha synuclein have pharmacological activity potentially useful for prophylaxis of synucleinopathic disease. Typically, inhibitory activity is determined by comparing levels of alpha synuclein and/or its fragments in medium from a cell treated with a test agent versus a comparable control cell not treated with the agent. As discussed in copending application U.S. Ser. No. 60/471,929 filed May 19, 2003, U.S. Ser. No. 10/850,570 filed May 19, 2004 and Ser. No. 10/969,335 filed Oct. 19, 2004, which is a CIP thereof, certain fragments of alpha synuclein with C-terminal truncations preferentially accumulate in Lewy bodies (e.g., SN1-119 and SN1-122). For example, media from PeakS cells transfected with alpha synuclein contain two prominent truncated species of about 12 and 7 kDa. Agents inhibiting processing reactions that form such fragments therefore have pharmacological activity useful for treating diseases characterized by Lewy bodies. The NAC fragment of alpha synuclein accumulates in extracellular amyloid deposits in Alzheimer's disease. Agents that inhibit formation or secretion of NAC therefore have pharmacological activity useful for treating Alzheimer's disease.

Suitable cells include cells transfected with nucleic acids encoding alpha synuclein, preferably, human alpha synuclein and cells naturally expressing alpha synuclein, also preferably human. The alpha synuclein in transfected cells can bear a mutation, such as S129A, S129D, A53T and A20P. Cells include PeakS cells, SY5Y cells, human cortical cells, human neuroglioma cell lines, human HeLa cells, primary human endothelial cells (e.g. HUVEC cells), primary human fibroblasts or lymphoblasts, primary human mixed brain cells (including neurons, astrocytes, and neuroglia), Chinese hamster ovary (CHO) cells, and the like. SY5Y cells are neuronal cells that can be induced to differentiate by treatment with retinoic acid/BDNF (brain derived neurotrophic factor). Transfected cells expressing alpha synuclein at higher levels than normal human cells are preferred. In some such cells, the alpha synuclein bears a mutation associated with synucleinopathic disease.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. The test compounds are typically administered to the culture medium at a concentration in the range from about 1 nM to 1 mM, usually from about 10 μM to 1 mM. Test compounds which are able to inhibit formation, processing or secretion of alpha synuclein are candidates for further determinations in transgenic animals and eventually human clinical trials.

C. Transgenic Animals

The antibodies of the invention and assays for detecting them can also be used to monitor alpha synuclein production, and processing in transgenic animal models of disease. Transgenic animal models of Lewy body disease are described by Masliah, et al. *Science* 287:1265-1269 (2000); Masliah et al., *PNAS USA* 98:12245-12250 (2001). Alpha synuclein can be analyzed either in body fluids as described above for human samples, or in tissue samples taken directly from the animal (see copending 60/423,012, filed Nov. 1, 2002, incorporated by reference). Tissue samples can be classified as Lewy body, particulate fraction and soluble fractions. Simple assays can be performed as for cell culture to screen agents for capacity to inhibit formation of alpha synuclein or its processing to fragments. Typically, the inhibitory activity is determined by comparing the level of alpha synuclein or a fragment thereof in a particularly body fluid or fraction from a tissue sample from a transgenic animal treated with the agent in comparison with the level of alpha synuclein or the fragment in the same body fluid or fraction in a control transgenic animal not treated with the agent. Inhibitory activity is shown by decreased levels of alpha synuclein of fragment thereof in the treated animal relative to the control.

Tissue samples from the brains of human patients can be subject to similar analyses. However, as obtaining samples from the brains of patient is an undesirably invasive procedure, such analyses are usually confined to cadavers. The analyses are useful, for example, in identifying fragments of alpha synuclein that preferentially accumulate in Lewy bodies, as described in copending application 60/471, 929, filed May 19, 2003 and its progeny supra.

V. Kits

The invention further provides kits including one or more antibodies of the invention. In some kits the antibodies are preimmobilized to a solid phase. For example, several different antibodies can be immobilized to the wells of a microtiter dish. Optionally, labeling reagents, such as an antiidiotypic antibody are also included in the kits. The labeling may also include a chart or other correspondence regime correlating levels of measured label with levels of antibodies to alpha-SN. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits. The kits can be sold, for example, as research or diagnostic reagents.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted.

EXAMPLES

I. Antibodies of the Invention

TABLE 1

| Antibody | ANTIGEN | Epitope Mapping (aa#) SEQ ID NO: 1 | Isotype | Specificity | Application |
|---|---|---|---|---|---|
| 7G4 (JH4) | bovine α- and β-synuclein | 109-120 | IgG2a | α | WB, H, IF |
| 6A8 | bovine α- and β-synuclein | 109-120 | IgG2b | α | WB, IP, H, IF |
| 5C12 | bovine α- and β-synuclein | 109-120 | IgG2b | α | WB, IP, ER, H, IF |
| 6A12 | bovine α- and β-synuclein | 109-120 | IgG2b | α | WB, IP, IF |
| 4B1 | bovine α- and β-synuclein | C-terminus | IgG2a | α β | WB |
| 8A5 | bovine α- and β-synuclein | C-terminus | IgG1 | α β | WB, IP, IF, poor EC |
| 6H7 (JH17) | recombinant human α-synuclein | N-terminus | IgG1 k | α β | WB, EC, ER |
| 3A12 | recombinant human α-synuclein | 43-51, 58-65 | IgG1 k | α β | WB, EC |
| 12C1 | recombinant human α-synuclein | 43-51, 58-65 | IgG1 k | α β | WB, EC, ER |
| 9A6 | recombinant human α-synuclein | 91-96 | IgG1 k | α β | WB, EC |
| 9G5 | recombinant human α-synuclein | 91-96 | IgG1 k | α | WB, EC |
| 9 E4 | recombinant human α-synuclein | 118-126 | IgG1 k | α, slight β | WB, EC (human specific) |
| 1H7 | recombinant human α-synuclein | 91-99 | IgG1 k | α | WB, EC |
| 23E8 (JH19) | VGSKTKEGVVHGVATVGGC (SEQ ID NO: 4) | 40-55 | IgG1 k | α β | WB, IP, EC |

TABLE 1-continued

| Antibody | ANTIGEN | Epitope Mapping (aa#) SEQ ID NO: 1 | Isotype | Specificity | Application |
|---|---|---|---|---|---|
| 10G5 (JH21) | EA(nitro Y)EMGGC (SEQ ID NO: 5) | 123-127 (nitrotyrl125) | IgG2a k | α β(?) | WB |
| 11A5 (JH22) | CAYEMP(phosphoS)EEGYQ (SEQ ID NO: 6) | 124-134 (phospho129) | IgG1 k | α | |
| ELADW-101 | CGGDMPVD (SEQ ID NO: 7) | 115-119 | | Neo-epitope | WB, IP, specificity, ELISA, H |
| 12C6 | CGGDMPVD (SEQ ID NO: 7) | 115-119 | IgG1 k | Neo-epitope | WB |
| ELADW-103 | PDNEAGGC (SEQ ID NO: 8) | 120-124 | | Neo-epitope | WB, IP, specificity, ELISA, H |

Abbreviations:
IP (immunoprecipitation);
H (histology);
EC and ER (ELISA capture and reporter antibody);
WB (western blot).,
IF immunofluorescence.

The antibodies were produced by immunizing with the antigen shown. Hybridomas were produced by standard methods, and tested for appropriate binding specificity.

II. ELISA Assays

Capture antibodies were biotinylation by a modification of the Igen commercial method. Pierce sulfo NHS biotin was prepared at 4 mg/ml in H2O and added at a 40 M excess to 1 mg/ml antibody in 150 mM KPO4 pH 7.8. This was incubated with gentle mixing in the dark for two hours and then dialyzed against PBS to remove free biotin. Capture antibodies were diluted to 10 μg/ml in Well Coating Buffer 0.1 M PO4. pH 8.5. Plates were coated 100 μl per well in Dynx 4HBX plates overnight at room temperature. Plates were then blocked in 0.25% Casein/PBS.

Standard curves of synuclein were prepared either in Specimen Diluent—(0.6% BSA, 0.05% Triton 405, 0.5% Thimerisol in 0.1 M PO4, 0.15 M NaCl pH 7.4) or 0.5 M guanidine, 0.25% casein/protease inhibitor/PBS depending on the samples to be assayed. Samples were diluted in either Specimen Diluent or the guanidine/casein depending on sample. Standards and samples were incubated over night at 4° C. For simple samples, room temperature and a few hours are sufficient. Plates were washed 4 times.

Plates were then incubated with the appropriate biotinylated antibody at 2 μg/ml in Specimen Diluent for 1 hour. Plates were washed 4 times. Plates were then incubated with Vector Strepavidin HRP 1/5000 or Amersham Strepavidin HRP at 1/10000 in Specimen Diluent at 100 μl/well for 1 hour. Plates were washed 4 times. BioFx TMB was added 100 μl/well and incubated 5 minutes at room temperature. The reaction was stopped with 100 μl BioFx stop and read on a Spectromax plate reader at 450 nm. Samples were assayed from the standard curve using the machine software and a 4 parameter curve fit.

ELISA assays were developed for the measurement of synuclein from various sources included human and rodent brain, cell culture and Lewy Body Preps. The follow table describes the sensitivity of various capture antibodies when 5C12 biotin is used as the reporter

TABLE 2

| Antibody | Epitope recognized | Sensitivity |
|---|---|---|
| 1H7 | 91-99 α specific | 100 pg/ml |
| 3A12 | 43-51 & 58-65 α/β | 300 pg/ml |
| 6H7 | N-terminus α/β | 7000 pg/ml |
| 9A6 | 91-96 α specific | 300 pg/ml |
| 9E4 | 118-126 α specific | Not done |
| 9G5 | 91-96 α specific | 1000 pg/ml |
| 12C1 | 43-51 & 58-65 α/β | 1000 pg/ml |
| 8A5 control | C-terminus α/β | 10,000 pg/ml |

1H17/5C12 was shown to have the best sensitivity in the above assays. 1H7 was then used as a plate coat to investigate if any other antibodies used as a reporter offered any increases in sensitivity. Table 3 describes the results.

TABLE 3

| Antibody | Epitope | Sensitivity |
|---|---|---|
| 3A12 | 43-51 & 58-65 α/β | Did not work |
| 6H7 | N-terminus α/β | 2200 pg/ml |
| 9A6 | 91-96 α specific | Did not work |
| 9E4 | 118-126 α specific, human specific | 750 pg/ml |
| 9G5 | 91-96 α specific | Did not work |
| 12C1 | 43-51 & 58-65 α/β | 2000 pg/ml |
| 5C12 | 109-120 α specific | 100 pg/ml |
| 8A5 | C-terminus | 2 ng/ml |

9A6 and 9G5 appeared to fail as a reporter due to cross blocking of the capture and reporter. The failure of 3A12 is due to poor biotinylation of the antibody and can be re-visited if needed.

From these results, the combination of 1H7 capture and 5C12 reporter for total synuclein in human samples is recommended. Although the 5C12 antibody binds to both mouse and human alpha synuclein, this is not a problem in human samples because no mouse synuclein is present. The combination of 1H7 capture 9E4 reporter for detecting human alpha synuclein in transgenic mouse brains is recommended. 9E4 is specific to human alpha synuclein. Both formats are specific for alpha-synuclein. The combination of 1H7 capture and 8A5 reporter is recommended for measurement of alpha synuclein having an intact C-terminus. The combination of 11A5 capture and 5C12 reporter is suitable for detecting alpha synuclein phosphorylated at residue 129. The combination of 1H7 as capture antibody and 11A5 as reporter offers about ten-fold greater sensitivity. The 11A5 antibody is specific for alpha synuclein phosphorylated at residue 129.

Figure 2:
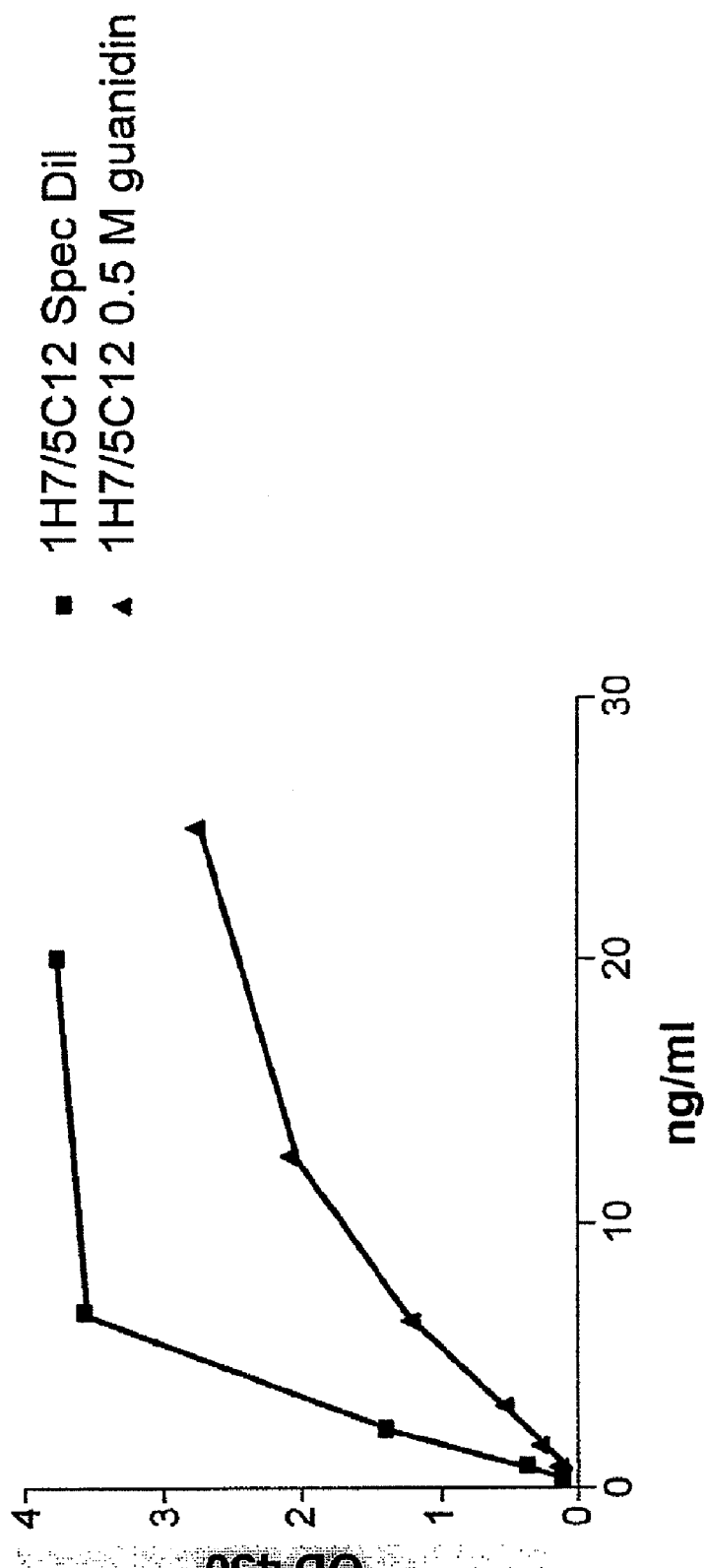
FIG. 2 shows a calibration curve for detection of alpha synuclein using 1H7/5C12 as capture and reporter antibodies. 1H7/5C12 is equal in sensitivity to 1H7/9E4 in 0.5 M guanidine.
Figure 3:
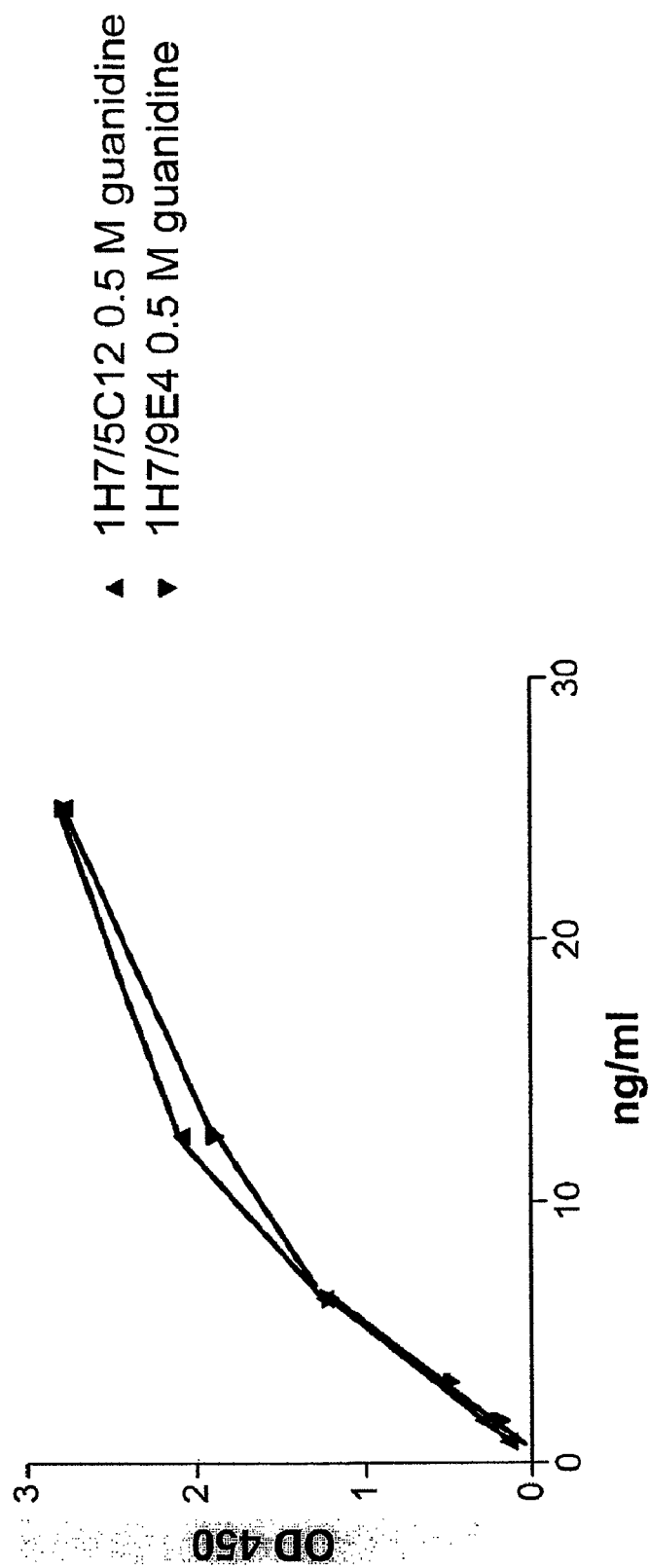
FIG. 3 shows a calibration curve for detection of alpha synuclein using 1H7 and 9E4 as capture and reporter antibodies. 1H7/9E4 is equal in sensitivity to 1H7/5C12 in 0.5 M guanidine.
Figure 4:
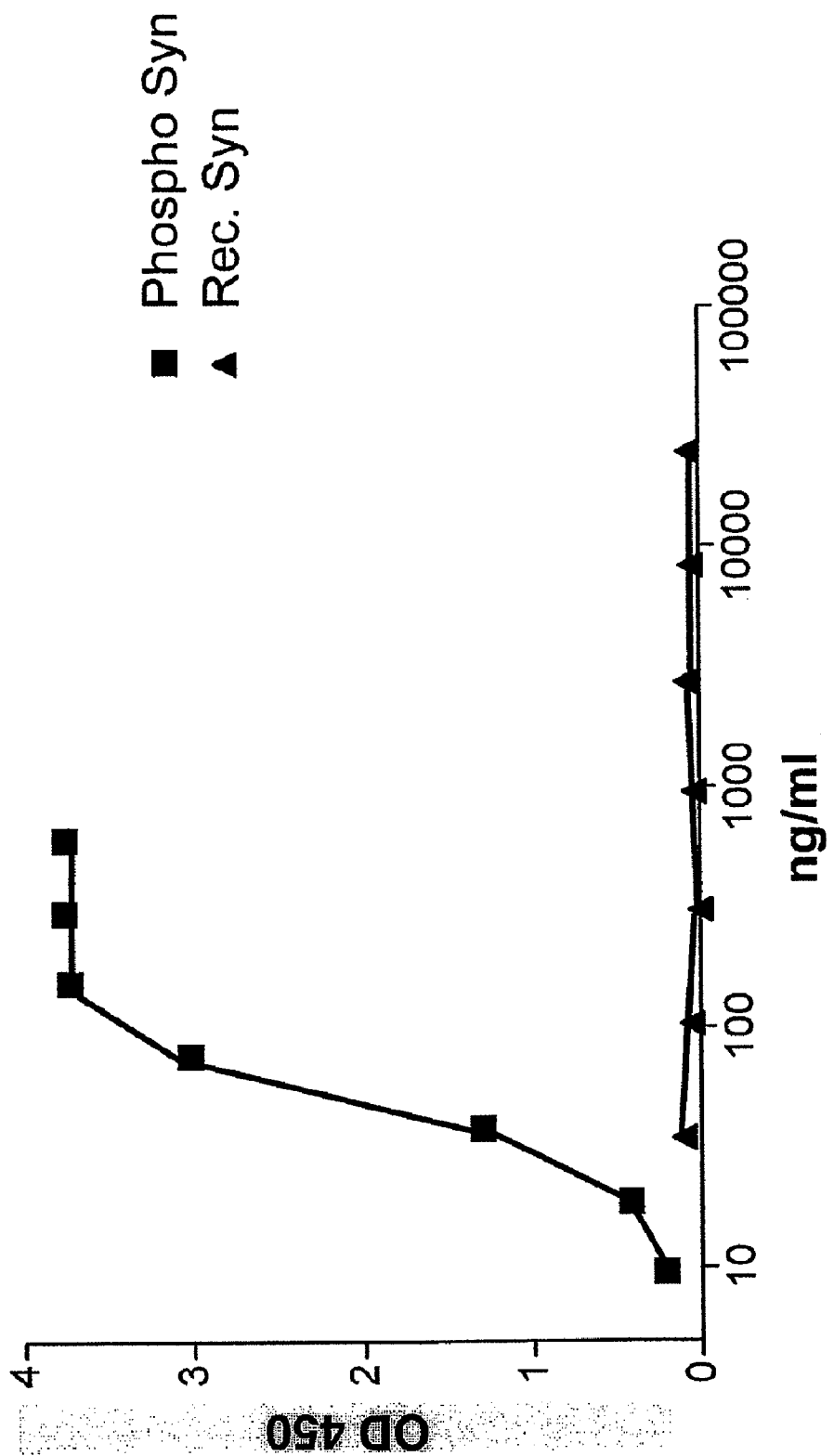
FIG. 4 shows a calibration curve for detection of phosphorylated alpha synuclein using 11A5 and 5C12 as capture and reporter antibodies.

A calibration curve showing OD450 vs. concentration of alpha synuclein using 1H7 and 5C12 as capture and reporter antibody is shown in FIG. 2. The assay is more sensitive in the absence of guanidine. A calibration curve for 1H7/9E4 in the presence of 0.5 M guanidine buffer is shown in FIG. 3. The guanidine maintains synuclein in a mildly denatured state making epitopes available for antibody binding and decreasing interactions with other proteins. FIG. 4 shows a calibration curve for the combination of 11A5/5C12 for detection of phosphorylated alpha synuclein. The actual sensitivity is about twenty fold greater than the measure value of 9 ng/ml because the alpha synuclein was only about 6% phosphorylated.

Figure 1B:
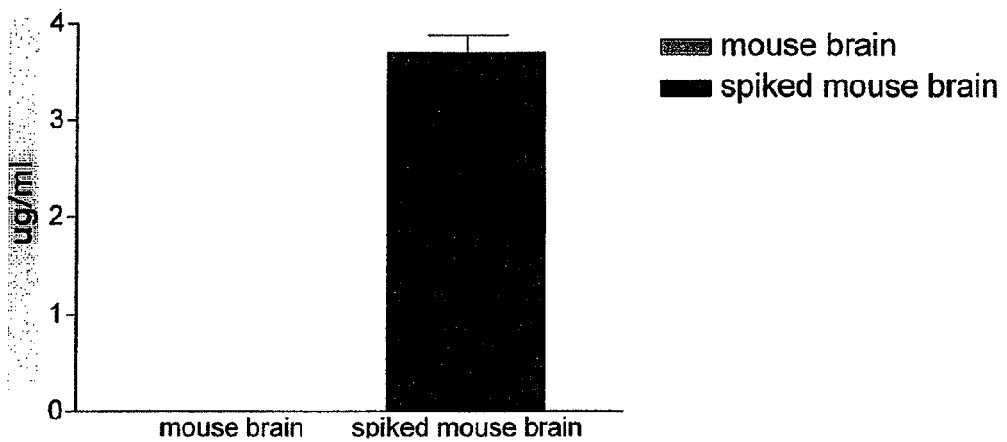

The capacity of the ELISA assay to quantify synuclein in a sample was testing by spiking brain homogenates from non-transgenic mice with known amounts of alpha synuclein. FIG. 1A shows the results using 1H7/5C12 as capture and reporter antibodies. The assay detects 96% of the added alpha synuclein. Some synuclein is detected in the control because the 5C12 antibody binds to both mouse and human alpha synuclein. FIG. 1B shows the results using 1H7 and 9E4 as capture and reporter antibody. In this case, no alpha synuclein is detected in the control because 9E4 binds to human alpha synuclein only. 92% of the added alpha synuclein was detected in the spiked sample, showing that detection is quantitative.

III. α-Synuclein Detection in Samples

The ELISA assay was used to detect alpha synuclein in soluble, particulate and Lewy body preparations from DLBD patients and controls. A brain homogenate was spun at 1000 g. The pellet was the source of Lewy bodies. These were prepared by Percoll gradient density fractionation, DNA digestion, and immunoaffinity purification using antibodies tagged with magnetic beads. Optionally, the alpha synuclein content of Lewy bodies can be enriched by stripping with the anionic detergent sarkosyl. The soluble and particulate fractions were prepared by spinning the initial supernatant at 150,000 g. The resulting supernatant was referred to as a soluble fraction, and the pellet as the particulate fraction. Synuclein can be extracted from these fractions using 0.5 and 5 M guanidine respectively. Note that the Lewy body samples were in UTC and that the soluble brain samples were prepared in Tris-buffered sucrose, and were assayed at a dilution in which these buffers did not interfere with the ELISA.

The soluble extract of the 8 human brains assayed contain approximately 0.03% of α-synuclein. There is a trend toward decreasing amounts of α-synuclein in the soluble brain fraction of a diseased patient. (Table 4). There is a statistically significant increase in the amount of synuclein in the particulate fraction of the DLBD brain (Table 5). The increased level of synuclein may be due to immature Lewy bodies that are to small to pellet with mature Lewy bodies in the initial centrifugation.

The amount of α-synuclein in the Lewy body prep varies. According to the 1H7/5C12 ELISA, synuclein comprises at most 0.07% of the total Lewy body protein.
The 1H7/9E4 ELISA measures approximately 60% less α-synuclein in the Lewy bodies than the 1H7/5C12 ELISA. The 9E4 reporter antibody recognizes an epitope more C-terminal than that of 5C12, and therefore the assay may simply reflect the presence of C-terminal truncations in the Lewy bodies as seen on 2-D gels. In this case loss of 9E4 reactivity or a lowered ratio of 9E4/5C12 activity (or other antibodies with the same or similar epitopes) is a marker of pathogenicity. Indeed, the 9E4 epitope encompasses the estimated cleavage sites. The soluble fraction contains less truncated synuclein and did show only a 12% difference between the ELISA assays consistent with this interpretation. An alternate explanation is that 9E4's epitope is modified or masked (perhaps due to the aggregation as described above or modification of tyrosine at 125) and cannot be detected.

TABLE 4

Soluble fraction

| | | ng α-Synuclein/ mg Protein | | |
|---|---|---|---|---|
| | Sample | 5C12 | 9 E4 | 9 E4/5C12 |
| Contr | N91/204 | 2089 | 1814 | 87% |
| | N92/290 | 1854 | 1535 | 83% |
| | N27 | 1218 | 1059 | 87% |
| | N28 | 1052 | 900 | 86% |
| | Mean | 1810 | 1540 | 86% |
| DLB | P23 | 761 | 669 | 88% |
| | P26 | 1068 | 921 | 86% |
| | P36 | 1150 | 967 | 84% |
| | P40 | 1381 | 1126 | 82% |
| | Mean | 1170 | 1060 | 85% |

TABLE 5

(α-Synuclein ELISA Results From Lewy Bodies)

| | | ng α-Synuclein/ mg Protein | | |
|---|---|---|---|---|
| | Sample | 5C12 | 9 E4 | 9 E4/5C12 |
| contr | N91/204 | 270 | 233 | 86% |
| | N91/290 | 222 | 193 | 87% |
| | N91/182 | 120 | 109 | 91% |
| | N92/001 | 259 | 210 | 81% |
| | N27 | 299 | 237 | 79% |
| | N28 | 289 | 248 | 86% |
| | Mean | 243 | 205 | 85% |
| DLB | P23 | 532 | 333 | 63% |
| | P26 | 366 | 264 | 72% |
| | P36 | 501 | 360 | 72% |
| | P40 | 319 | 259 | 81% |
| | Mean | 429 | 304 | 72% |

TABLE 6

Alpha synuclein in Lewy bodies

| | ng α-Synuclein/ mg Protein | | |
|---|---|---|---|
| Sample | 5C12 | 9 E4 | 9 E4/5C12 |
| P36A | 7596 | 2442 | 32% |
| P36A | 7413 | 1587 | 21% |
| P40A | 561 | 180 | 32% |
| P40A | 557 | 206 | 37% |
| P50A | 3836 | 823 | 21% |
| P50A | 3761 | 896 | 24% |
| Mean | 3954 | 1022 | 28% |

Detection of α-Synuclein in Blood

Blood samples from four healthy volunteers were collected into both EDTA- and heparin-containing tubes and plasma samples were prepared. The plasma was initially diluted 2-fold with 1M guanidine for a final concentration of 0.5 M guanidine. Samples were assayed in 1H7/5C12 ELISA assay using the standard buffer of 0.25% casein, 0.5 M guanidine, and protease inhibitors plus 300 μg/ml mouse IgG (added to prevent interference from a human anti-mouse response that can be quite common in patient samples).

Plasma from the EDTA collection gave excellent spike and recovery of α-synuclein. The amount of synuclein varied almost 2-fold between patients. The amount of synuclein in the heparin collected plasma was up to 10-fold lower than that of the EDTA collected plasma. Not only was the total α-synuclein concentration lower but so was the spike and recovery indicating that heparin interferes with the assay possibly by binding to synuclein. In all further experiments, EDTA collection tubes were used.

The presence of synuclein in the plasma indicates that it is produced in cells from the blood. Secretion is unlikely because synuclein is not a secreted protein. Release during cell breakage is more likely. Which cells in the blood, i.e. white blood cells (WBC), red blood cells (RBC), and platelets produce synuclein was investigated. To prepare WBC, whole blood was spun down at 1000×g and the plasma removed. The packed cell pellet was washed two times at 300×g to remove any platelet contamination. The RBC were lysed in de-ionized water for 1 minute and the sample was readjusted to 1×PBS. There was a small amount of RBC contamination. The resulting pellet was homogenized in 5 M guanidine, diluted 1/10 in assay buffer, treated with DNAse, and then spun in the microfuge to remove insoluble material.

In an alternate fractionation, blood was processed to generate total blood cells, platelets and plasma. The blood was spun at 350×g to pellet cells but not platelets. The plasma was removed and spun at 1000×g to remove platelets. The cell pellet was washed two times at 350×g to remove any remaining platelets. Both plasma and cells were initially diluted/homogenized in 5 M guanidine. The cell pellet was further diluted 1:10, treated with DNAse and spun to remove insoluble material. To test the synuclein specificity of the ELISA, an aliquot of the platelet and the total blood cell samples were absorbed with the synuclein antibody 1H7 coupled to Sepharose.

The amount of synuclein measured in whole blood is too large to be accounted for by platelets or by WBC as previously shown, thus strongly suggesting that RBC, the most abundant cells in the blood, are the major source of synuclein in blood.

All samples (except plasma) were assayed for spike and recovery and well as % synuclein absorbable with 1H7 resin. In addition, all samples were run in the phospho-synuclein assay.

TABLE 7

| Sample | ng/ml Synuclein | ng/ml PO4-Syn | % Spike Recovered | % Absorbable |
|---|---|---|---|---|
| Whole Blood | 22000 | 132 | 92 | 64 |
| Platelets | 152 | 0.91 | 115 | 68 |
| WBC | 1.96 | BLD | 84 | 84 |
| Platelet Free Plasma | 10.8 | BLD | ND | ND |
| Platelet Rich Plasma | 63.3 | BLD | ND | ND |

The results confirm that low levels of synuclein are present in plasma and that low levels are also present in the cellular components of blood, WBC and platelets, leaving only the RBC unaccounted for. Thus by subtractive analysis, greater than 99% of the synuclein in blood resides in the RBC, with most of the remaining synuclein residing in the platelets. Less than 1% of the synuclein was phosphorylated in the 1H7/11A5 assay. The spike and recoveries were very good in all but the WBC prep. The absorption of synuclein by 1H7-conjugated Sepharose was not as robust as in the previous experiment but nonetheless indicated that the majority of the ELISA signal could be removed with a synuclein-specific antibody and therefore was likely due to synuclein.

The large amount of synuclein in RBC makes it difficult to accurately assess the amount of synuclein in plasma and WBC. A minor amount of contamination or lysis of RBC will greatly elevate the concentration found in these compartments. Platelets are difficult to work with in a clinical setting since all manipulations must be done within several hours of blood collection. In addition, platelets are notorious for activating even under the best of assay circumstances. Therefore the most practical measure of synuclein in blood is from total blood cells.

What is claimed is:

1. A hybridoma producing a monoclonal antibody selected from the group consisting of 6H7, 8A5, 9E4, and 1H7.

2. A humanized or chimeric version of a monoclonal antibody selected from the group consisting of 6H7, 8A5, 9E4, and 1H7.

3. The antibody of claim 2, wherein the antibody has an isotype of human IgG1.

4. The humanized or chimeric antibody of claim 2, wherein the antibody has the CDRs of monoclonal antibody 6H7.

5. The humanized or chimeric antibody of claim 2, wherein the antibody has the CDRs of monoclonal antibody 8A5.

6. The humanized or chimeric antibody of claim 2, wherein the antibody has the CDRs of monoclonal antibody 9E4.

7. The humanized or chimeric antibody of claim 2, wherein the antibody has the CDRs of monoclonal antibody 1H7.

8. A method of humanizing a donor monoclonal antibody selected from the group consisting of 6H7, 8A5, 9E4, and 1H7, comprising:
    providing a DNA encoding the variable domains of a donor antibody selected from the group consisting of 6H7, 8A5, 9E4, and 1H7;
    determining the amino acid sequence of the CDR regions of the donor monoclonal antibody from the DNA;
    selecting human acceptor antibody sequences; and
    producing a humanized antibody comprising the CDRs from the donor antibody and variable region frameworks from the human acceptor antibody sequences, optionally wherein one or more variable region framework residues from the human acceptor antibody sequences are substituted.

9. A method of producing a chimeric form of a monoclonal antibody selected from the group consisting of 6H7, 8A5, 9E4, and 1H7 comprising:
    providing DNA encoding the variable domains of a monoclonal antibody selected from the group consisting of 6H7, 8A5, 9E4, and 1H7;
    determining the amino acid sequence of the light and heavy chain variable regions of the monoclonal antibody from the DNA;
    selecting heavy and light chain constant regions from an acceptor antibody;
    producing a chimeric antibody comprising a light chain comprising the light chain variable region of the monoclonal antibody fused to the light chain constant region, and a heavy chain comprising the heavy chain variable region of the monoclonal antibody fused to the heavy chain constant region.

* * * * *

SEQUENCE LISTING

```
<160> NUMBER OF SEQ ID NOS: 8

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80
```

```
Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 35
<212> TYPE: PRT
<213> ORGANISM: Homo sapiens

<400> SEQUENCE: 2

Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
            20                  25                  30

Gly Phe Val
        35

<210> SEQ ID NO 3
<211> LENGTH: 28
<212> TYPE: PRT
<213> ORGANISM: Homo sapiens

<400> SEQUENCE: 3

Lys Glu Gln Val Thr Asn Val Gly Gly Ala Val Val Thr Gly Val Thr
1               5                   10                  15

Ala Val Ala Gln Lys Thr Val Glu Gly Ala Gly Ser
            20                  25

<210> SEQ ID NO 4
<211> LENGTH: 19
<212> TYPE: PRT
<213> ORGANISM: Artificial
<220> FEATURE:
<223> OTHER INFORMATION: Antigen

<400> SEQUENCE: 4

Val Gly Ser Lys Thr Lys Glu Gly Val Val His Gly Val Ala Thr Val
1               5                   10                  15

Gly Gly Cys

<210> SEQ ID NO 5
<211> LENGTH: 8
<212> TYPE: PRT
<213> ORGANISM: Artificial
<220> FEATURE:
<223> OTHER INFORMATION: Antigen
<220> FEATURE:
<221> NAME/KEY: MOD_RES
<222> LOCATION: (3)..(3)
<223> OTHER INFORMATION: Nitrogenated tyrosine

<400> SEQUENCE: 5

Glu Ala Xaa Glu Met Gly Gly Cys
1               5

<210> SEQ ID NO 6
<211> LENGTH: 12
<212> TYPE: PRT
```

```
<213> ORGANISM: Artificial
<220> FEATURE:
<223> OTHER INFORMATION: Antigen
<220> FEATURE:
<221> NAME/KEY: MOD_RES
<222> LOCATION: (7)..(7)
<223> OTHER INFORMATION: Phosphorylated serine

<400> SEQUENCE: 6

Cys Ala Tyr Glu Met Pro Xaa Glu Glu Gly Tyr Gln
1               5                   10

<210> SEQ ID NO 7
<211> LENGTH: 8
<212> TYPE: PRT
<213> ORGANISM: Artificial
<220> FEATURE:
<223> OTHER INFORMATION: Antigen

<400> SEQUENCE: 7

Cys Gly Gly Asp Met Pro Val Asp
1               5

<210> SEQ ID NO 8
<211> LENGTH: 8
<212> TYPE: PRT
<213> ORGANISM: Artificial
<220> FEATURE:
<223> OTHER INFORMATION: Antigen

<400> SEQUENCE: 8

Pro Asp Asn Glu Ala Gly Gly Cys
1               5
```